United States Patent [19]

Chen

[11] Patent Number: 5,840,720
[45] Date of Patent: Nov. 24, 1998

[54] 4-O AND 5-AMINOMETHYLATION OF SYNTHETIC CAPSAICIN DERIVATIVES, A NEW DISCOVERY OF CAPSAICIN ANTAGONIST

[75] Inventor: Ing-Jun Chen, Kaohsiung, Taiwan

[73] Assignee: Tong-Ho Lin, Taipei, Taiwan

[21] Appl. No.: 547,040

[22] Filed: Oct. 23, 1995

[51] Int. Cl.[6] .................................................. C07D 273/01
[52] U.S. Cl. ......................................... 544/230.5; 544/90
[58] Field of Search ............................. 544/90; 514/230.5

[56] References Cited

U.S. PATENT DOCUMENTS 3,082,112  3/1963  Hemwall .................................... 544/90
4,035,363  7/1977  Oka et al. ................................... 544/90

OTHER PUBLICATIONS

Ruthenium red antagonism of the effect of capsaicin on the motility of the isolated guinea–pig ileum, Takaki, Jin, and Nakayama, European Journal of Pharmacology, 174 (1989).

(List continued on next page.)

Primary Examiner—Donald G. Daus
Attorney, Agent, or Firm—Beveridge, DeGrandi, Weilacher & Young LLP

[57] ABSTRACT

A series of 4-O & 5-aminomethylation of synthetic capsaicin derivatives selectively reveal antagonist activity on capsaicin-sensitive sensory neurons, and inhibit its innervating atrium, airway, and ileum smooth muscles in vitro. The compound of this invention has the following formula

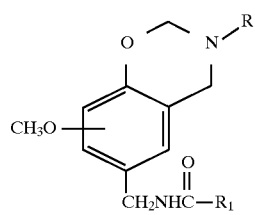

wherein R is a member selected from the group consisting of

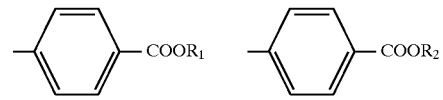

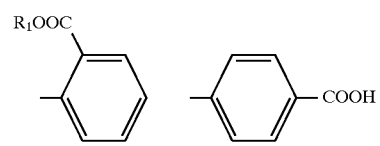

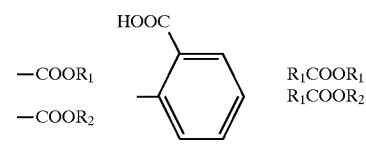

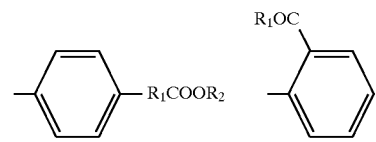

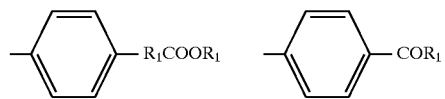

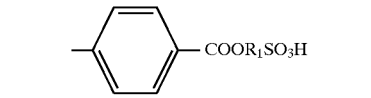

wherein $R_1$ is a member selected from the group consisting of $C_{1-12}$ alkyl, $C_{1-12}$ alkenyl, $C_{1-12}$ alkylene, and $C_{1-12}$ alkenylene, and wherein $R_2$ is a member selected from the group consisting of H, $C_{1-3}$ alkylene-$NR_1R_1$, and $C_{1-6}$ alkenylene-$NR_1R_1$.

10 Claims, 19 Drawing Sheets

Capsaicin ( cap ; A )
8-methyl-N-vanillyl-nonenamide

Nonivamide ( NVA ; B )
nonanoyl vanillylamide

OTHER PUBLICATIONS

Capsazepine inhibits low pH– and lactic acid–evoked release of calcitonin gene–related peptide from sensory nerves in guinea–pig heart, Cereceda and Lundberg, European Journal of Pharmacology, 221 (1992).

Ruthenium–red inhibits CGRP release by capsaicin and resiniferatoxin but not by ouabain, bradykinin or nicotine in guinea–pig heart: correlation with effects on cardiac contractility, Cereceda, Lou, and Lundberg, Br. J. Pharmacol. (1991).

A comparison of capsazepine and ruthenium red as capsaicin antagonists in the rat isolated urinary bladder and vas deferens, Maggi, Bevan, Walpole, Rang, and Giuliani, Br. J. Pharmacol. (1993).

Capsaicin ( cap ; A )
8-methyl-N-vanillyl-nonenamide

Nonivamide ( NVA ; B )
nonanoyl vanillylamide

4-O AND 5-AMINOMETHYLATION OF SYNTHETIC CAPSAICIN DERIVATIVES, A NEW DISCOVERY OF CAPSAICIN ANTAGONIST

TECHNICAL FIELD OF THE INVENTION

The present invention relates to new and useful capsaicin antagonist derivatives, especially to 4-O & 5-aminomethylation of synthetic capsaicin derivatives, and other 3-methoxy, 4-hydroxy compounds.

BACKGROUND OF THE INVENTION

Capsaicin is the principle of Capsium annuum Linne, a medicinal plant of Solanaceae. Capsaicin-sensitive functional change has been found in cardia, aorta, trachea, and animal tissues (Maggi & Meli, 1988). Capsaicin has been shown to have potent positive chronotropic and inotropic effects when applied to isolated guinea-pig atria (N. Fukada & M. Fumjiwara et al., J. Pharmacol. 21, 622–24, 1969; J. Molnar et al., Acta Physiolo. Acad. Sci Hung. 35, 369–74. 1969).

The contraction effect of capsaicin on the isolated guinea-pig ileum was suggested to be caused by parasympathetic transmission due to SP (substance P) release (L. A. Chahl, Naunyn-schmiedebergs Arch. Pharmacol. 310, 212–15, 1982). Capsaicin has been reported to inhibit neuronal sodium currents (K. Yamanaka et al., Brain Res. 300, 113–9, 1984) also inhibit neuronal calcium currents (M. Petersen et al., Pflvgers Arch. 409, 403–10, 1987). The capsaicin-sensitive effects on the functions of various tissues, including ileum smooth muscles, cardia muscles, and airways are known to be caused by the activation of sensory C-fibres (C. A. Maggi et al., Gen. Pharmacol. 19, 1–43,1988). The positive inotropic action of capsaicin is believed to be associated with the release of CGRP (calcitonin gene-related peptide) from intracardiac neurons, and has shown that capsaicin and CGRP prolong action potential duration in guinea pig atria (Franco-Cereceda et al., Acta Physiol. Scand. 132, 181–90, 1988).

The effects of capsaicin on rat urethra, urinary bladder, gastrointestinal, renal pelvis, genitourinary tract, and ureters have been reviewed by C. A. Maggi, et al.(Gen. Pharmacol. 19, 1–43, 1988). The activation of this proton-gated cation conductance allows sodium, calcium, and potassium ion to flow down its concentration gradient into the dorsal root ganglion cells causing depolarization and action potential generation (C. A. Forbes et al., Soc. Neurosci. Abstract. 14, 642. 1988). The inhalation of capsaicin can be used to increase airway resistance and leads to bronchoconstriction (J. G. Collier et al., Br. J. Pharmacol. 81, 113–7, 1984).

The synthetic capsaicin derivatives with cardioinhibitory and antibronchoconstrictory properties have rarely been described. Capsazepine 2[4-chlorphenyl) ehtylaminothiocarbonyl]-7, 8-dihydroxy-2, 3, 4, 5-tetrahydro-1-H-2-benzazepine), first synthesized by Whalloe et al. (Br. J. Pharmacol. 107, 544–552, 1992) as an antagonist of capsaicin (S. Bevan et al., Br. J. Pharmacol. 107, 544–52, 1992), was found to be effective in inhibiting the contractile response evoked by capsaicin or by electrical field stimulation in guinea-pig bronchi (M. G. Belvisi et al., Eur. J. Pharmacol. 215, 341–344, 1992). Capsazepine, chemically with a bicyclic benzazepine moiety similar to the bezodiazepine moiety of diazepam which is effective in inhibiting GABA receptor hypothesized locating on preterminal region of capsaicin-sensitive sensory nerves (D. A. Brown et al., Brain Rev. 156, 187–91, 1978), has been evaluated as a competitive capsaicin antagonist (S. Bevan et al., 1992). Our previous product, glyceryl nonivamide, was also proven to be a selective capsaicin agonist (I. J. Chen et al., Eur. J. Med. Chem. 27, 187–92, 1992). The positive results of S. Bevan et al. (1992) have encouraged us to search for other new capsaicin antagonist.

Previous studies on the structure-activity relationship of nonivamide (N-nonanoyl vanillylamide), the synthetic capsaicin, indicated that substitution for the OH group of capsaicin or nonivamide may lead to less pungency in the capsaicin derivatives (I. J. Chen et al. (1992)), including a non-pungent beta adrenergic blocker derivative with cardiotonic and CGRP releasing properties (I. J. Chen et al., J. Med. Chem. 37, 938–43, 1994). In a similar way, a series of 4-O & 5-aminomethylation of capsaicin derivatives (FIG. 1) another bicyclic capsaicin derivative like capsazepine, was first synthesized by a chemical reaction both masking the phenolic OH of and bicyclic nonivamide with a series of amino benzyl and amino alkyl compounds.

DETAILED DESCRIPTION

The present invention describes a series of 4-O & 5-aminomethylated capsaicin derivatives which have the formula A:

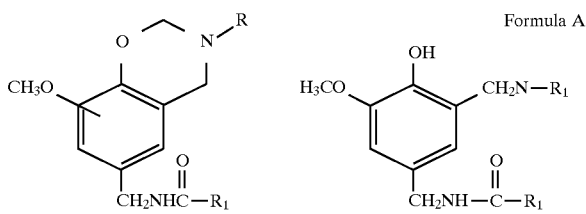

Wherein R is

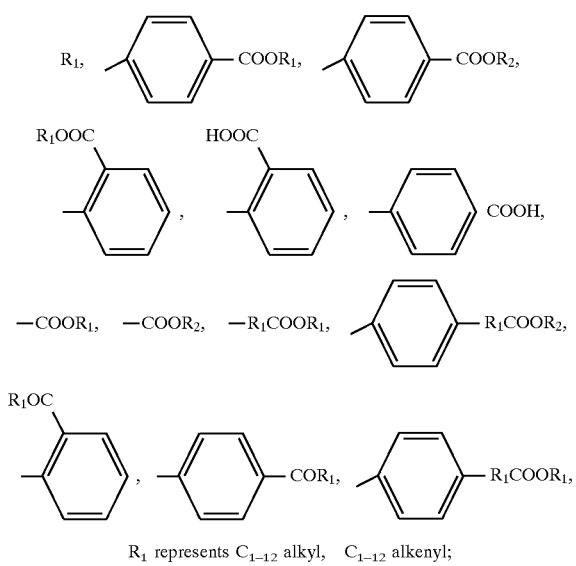

$R_1$ represents $C_{1-12}$ alkyl, $C_{1-12}$ alkenyl;

$R_2$ represents H, $C_{1-6}$—$NR_1R_1$.

I. Methods of Preparation

Figure 1:
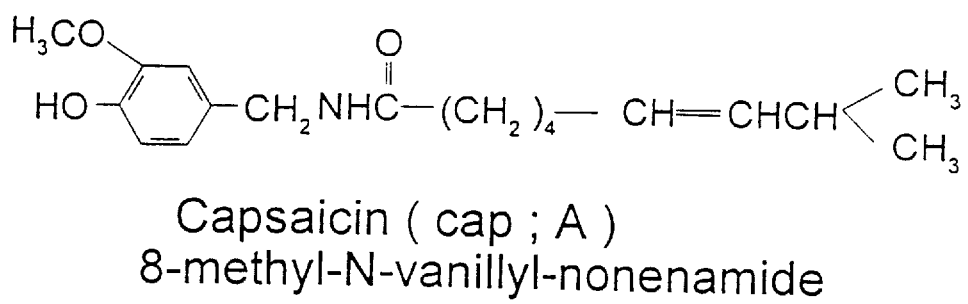
FIG. 1 Chemical structures of capsaicin and nonivamide
Figure 1:
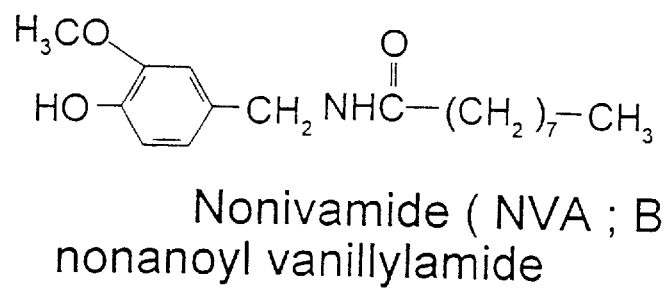

The methods of preparation for this invention (formula A) was shown in the section of Synthesis and Its Scheme (IV) in Schemes 1–4. The methods might be performed using amino benzyl, amino alkyl, amino phenylacetic acid, 4-aminopropiophenone and anthranilic acid compound and their esters to react with N-nonanoylvanillylamide (NVA) or other substituted guaiacol compounds via the Mannich reaction to give 4-O- and 5-amino-methylated derivatives of capsaicin or other guaiacol compounds (Formula A and FIG. 1).

The other methods of preparation comprise reacting NVA (N-nonanoylvanillylamide) or other guaiacol derivatives with dialkylamine to give 4-guaiacolic and 5-aminomethylated compounds (e.g. Compound 4, Scheme 4) via Mannich reaction as described shown in Formula A and Scheme of Synthesis Section (IV), Schemes 1–4.

In the invention of novel capsaicin derivative compounds most of the reacting materials were first amine, second amine, and/or substituted with straight or branched alkyl, straight or branched alkenyl. The guaiacoxyl group compounds including 4-O- and 5-aminoethylated capsaicin (CAP) nonvamide and other guaiacol derivatives were substituted with straight or branched alkyl group, alkenyl group. These structures of compounds of formula A described above were assigned according to the $^1$H-NMR, IR, MS, elemental analytical data, $^{13}$C-NMR.

II. Pharmacological Activity

A. Antagonist activity of compounds on capsaicin-induced contractility of isolated guinea-pig bronchi and trachea Adult guinea pigs (Hartley), weighing 350–450 g, were sacrificed by a blow on the head followed by cervical dislocation. The bronchi and trachea were removed from the lungs, cleaned of all parenchyma, and immediately placed in Kreb's solution. As the method reported by M. G. Belvisi et al. (Eur. J. Pharmacol. 215, 341–4, 1992).

Figure 2A:
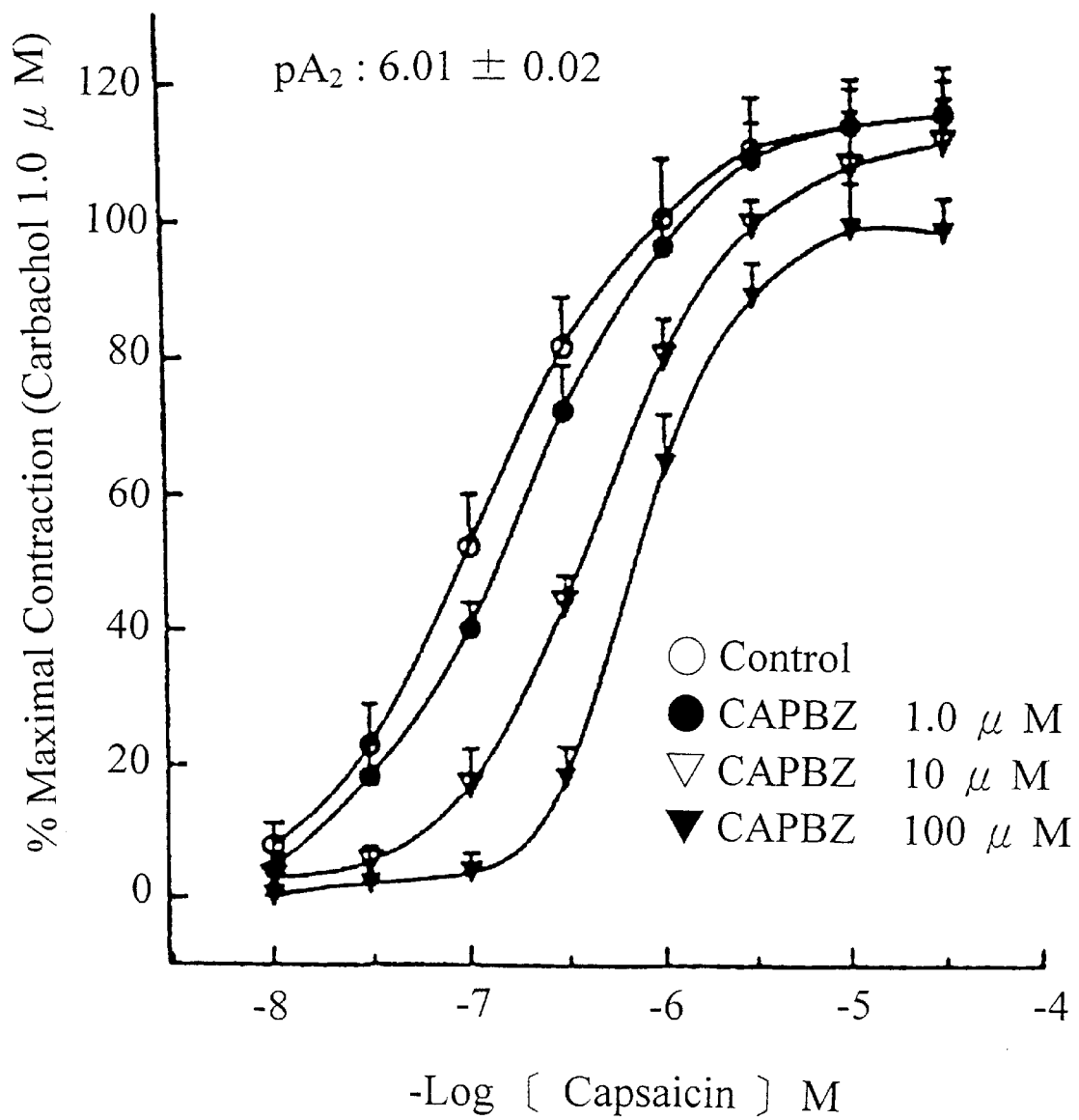
FIGS. 2A–2C Cumulative concentration-response curves to capsaicin ($10^{-9}$–$10^{-5}$M) in the absence and presence of CAPBZ and NVABI in the isolated guinea-pig trachea, expressed as a % of the maximum contraction to carbachol (1 $\mu$M). Each point represents mean±S.E.M of six experiments.
Figure 2B:
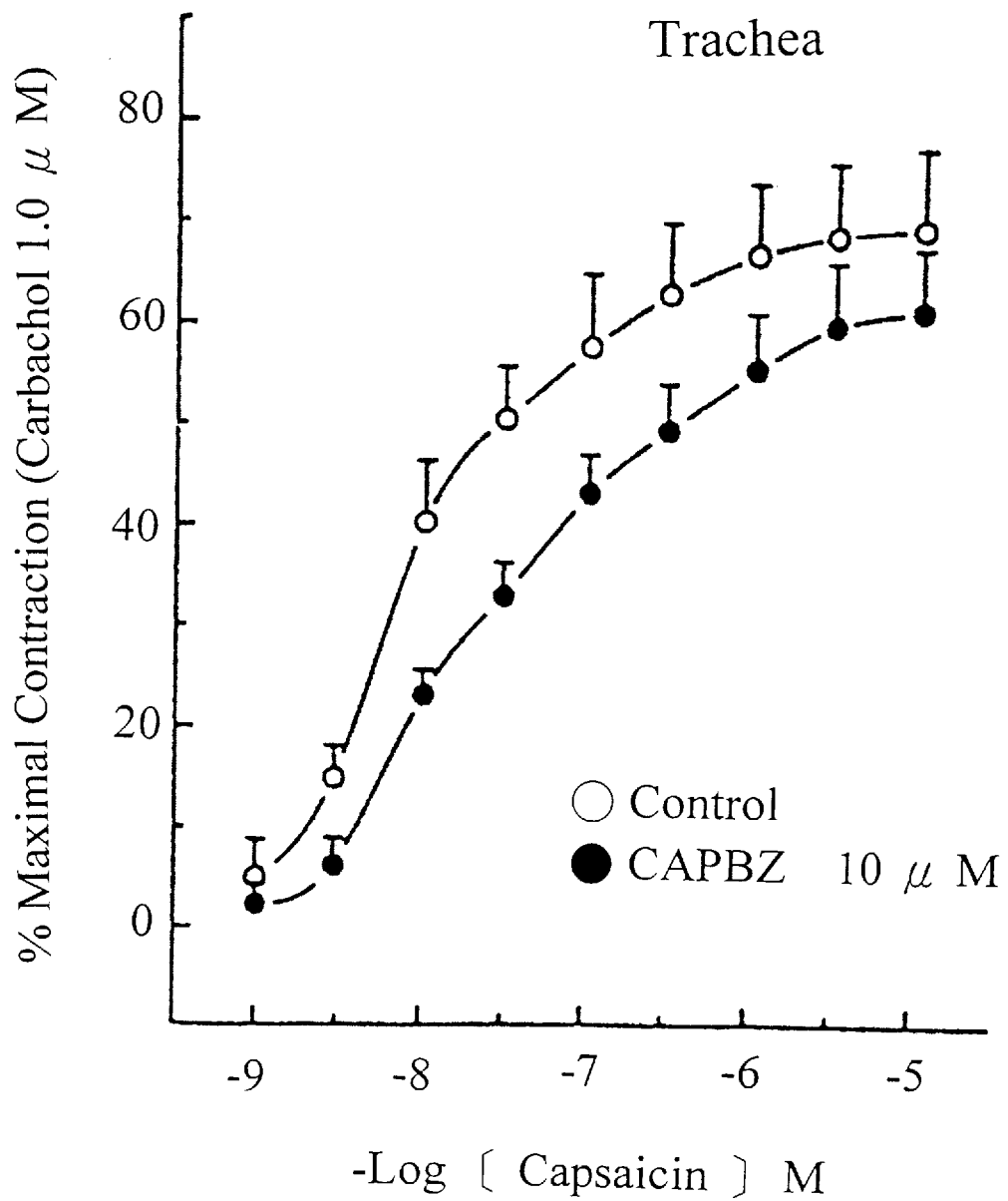
Figure 2C:
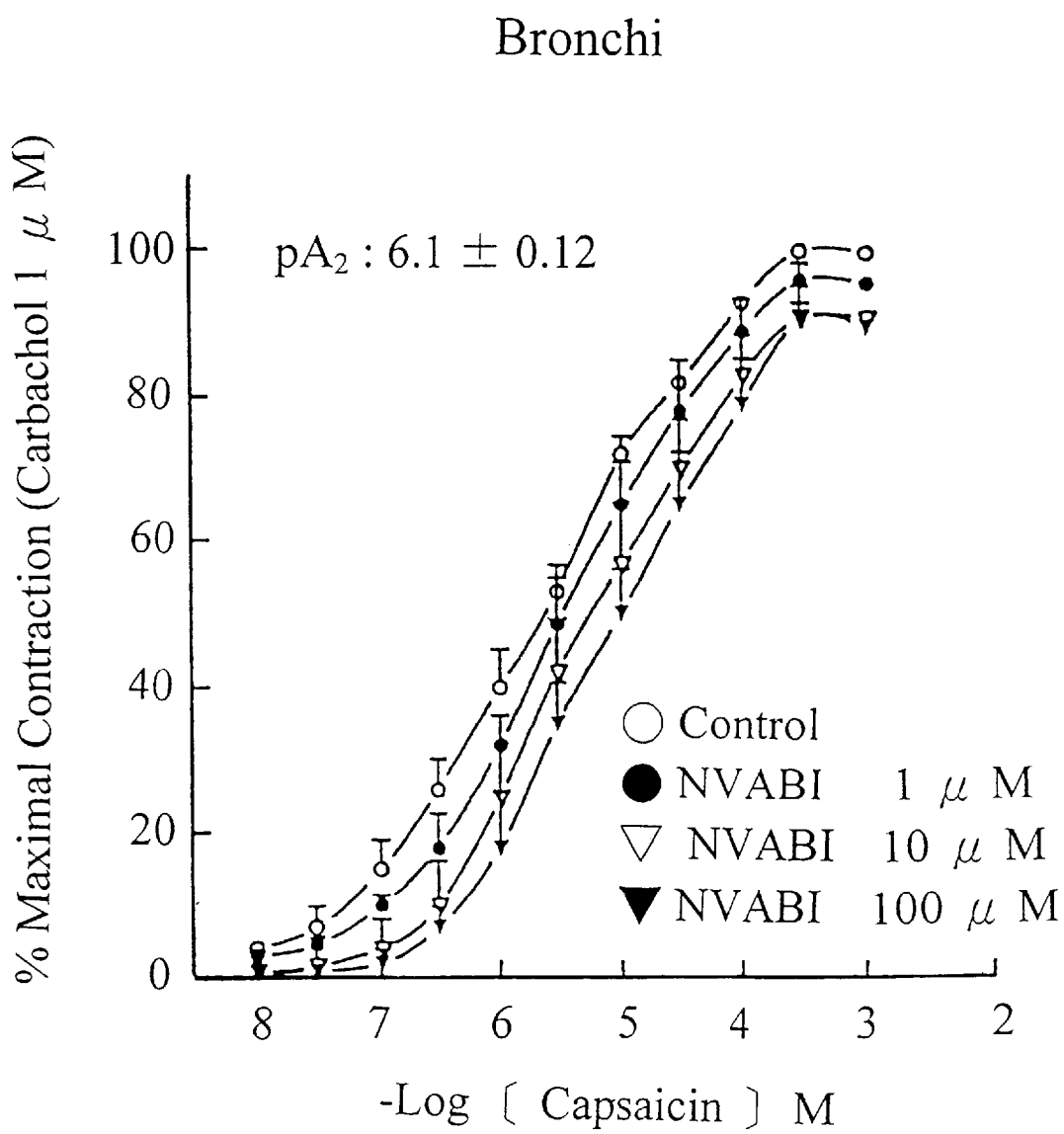
Figure 3A:
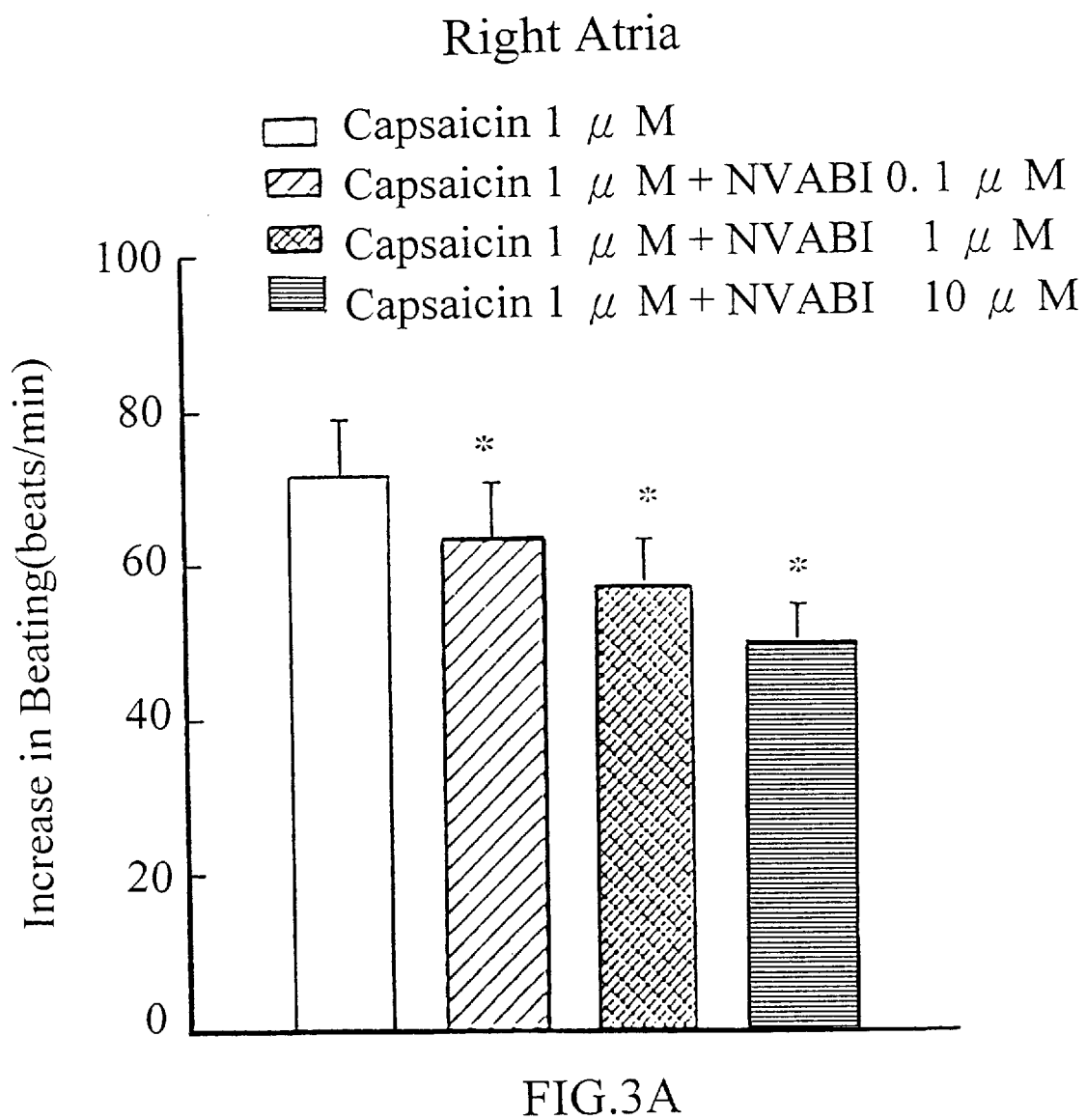
FIGS. 3A–3D Capsaicin (1 $\mu$M) caused a positive inotropic and chronotropic response on spontaneously beating guinea-pig right atrium and electrically-driven guinea-pig left atrium. CAPBZ and NVABI pretreatment for 30 min decreased the effect of capsaicin. Each data was the mean±S.E.M. of six experiments (*P<0.05. **P<0.01, Student's t-test)
Figure 3B:
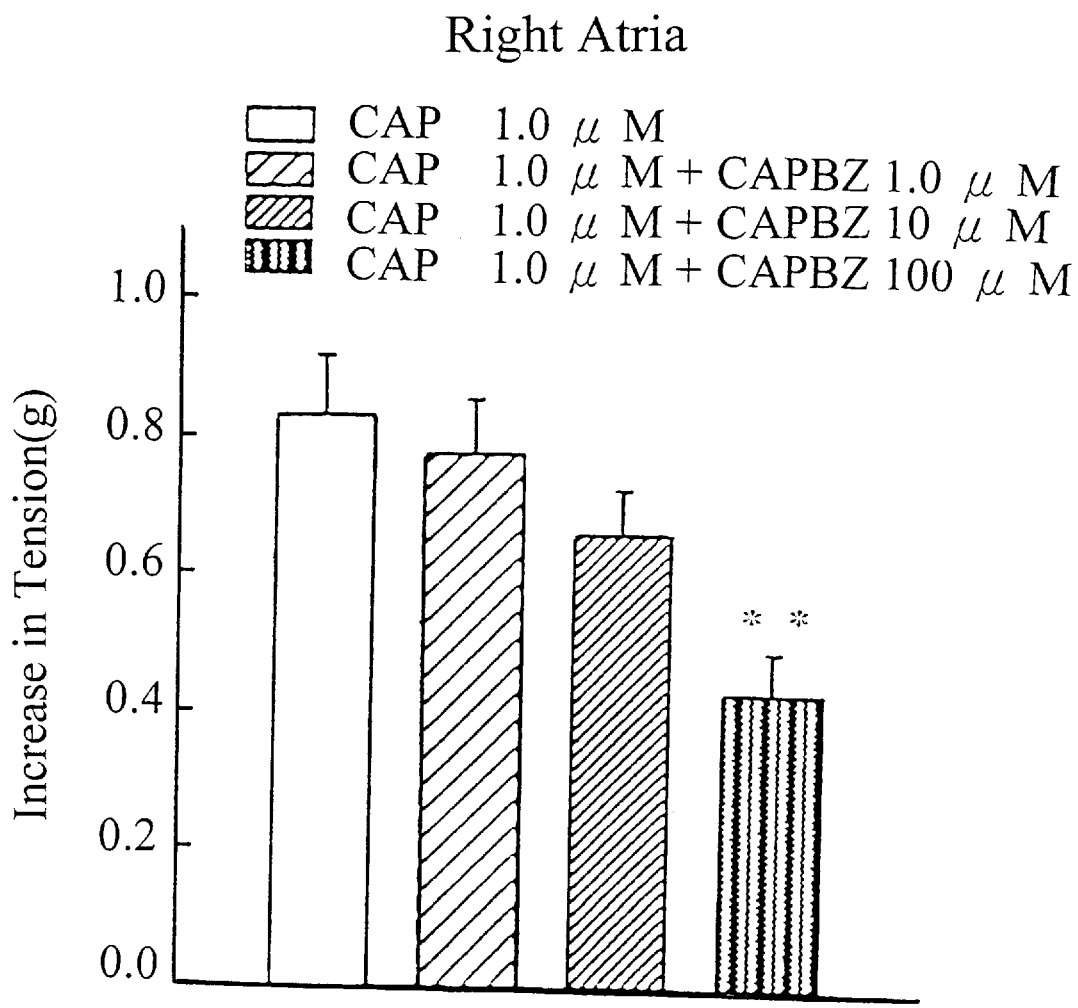
Figure 3C:
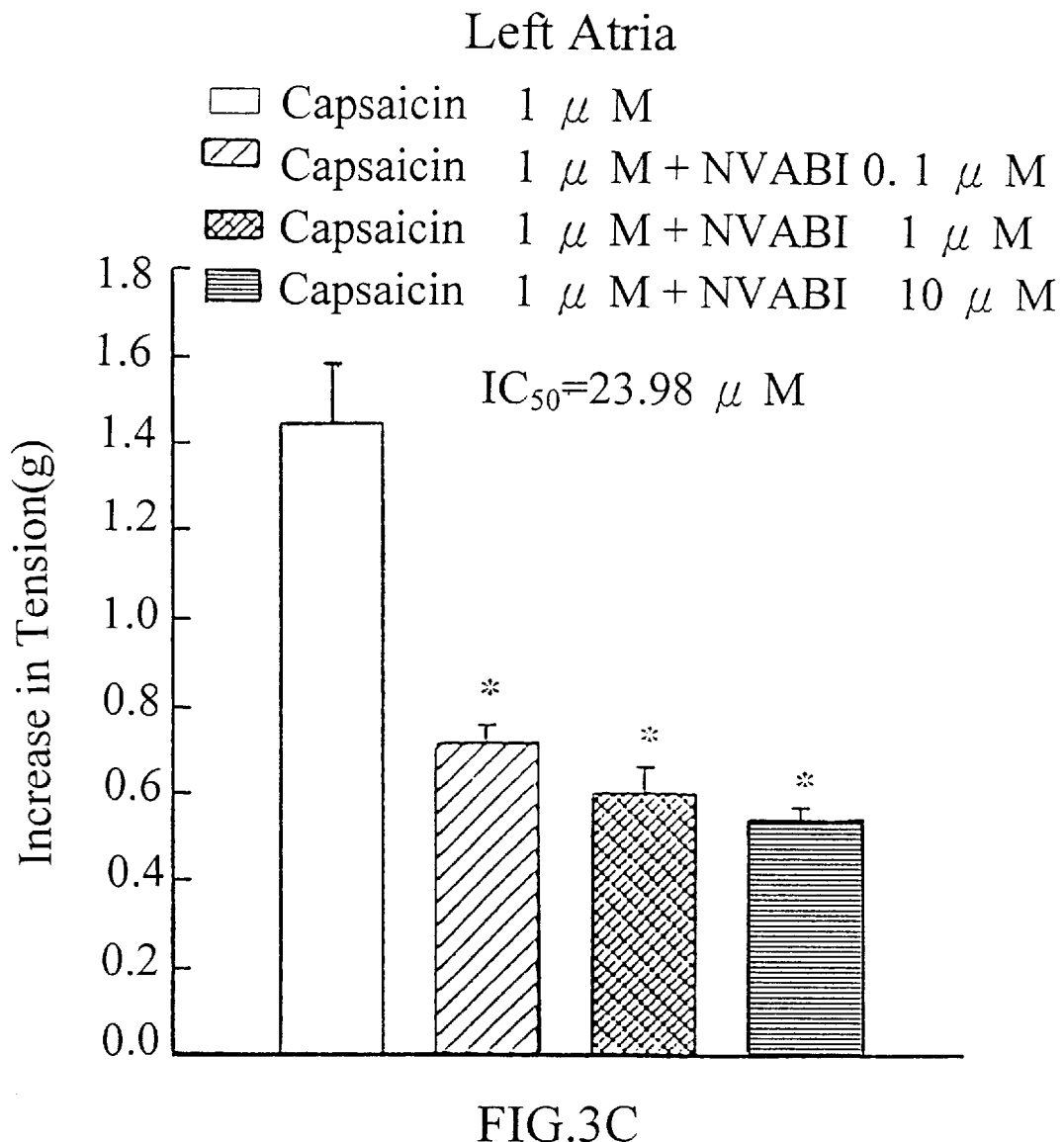
Figure 3D:
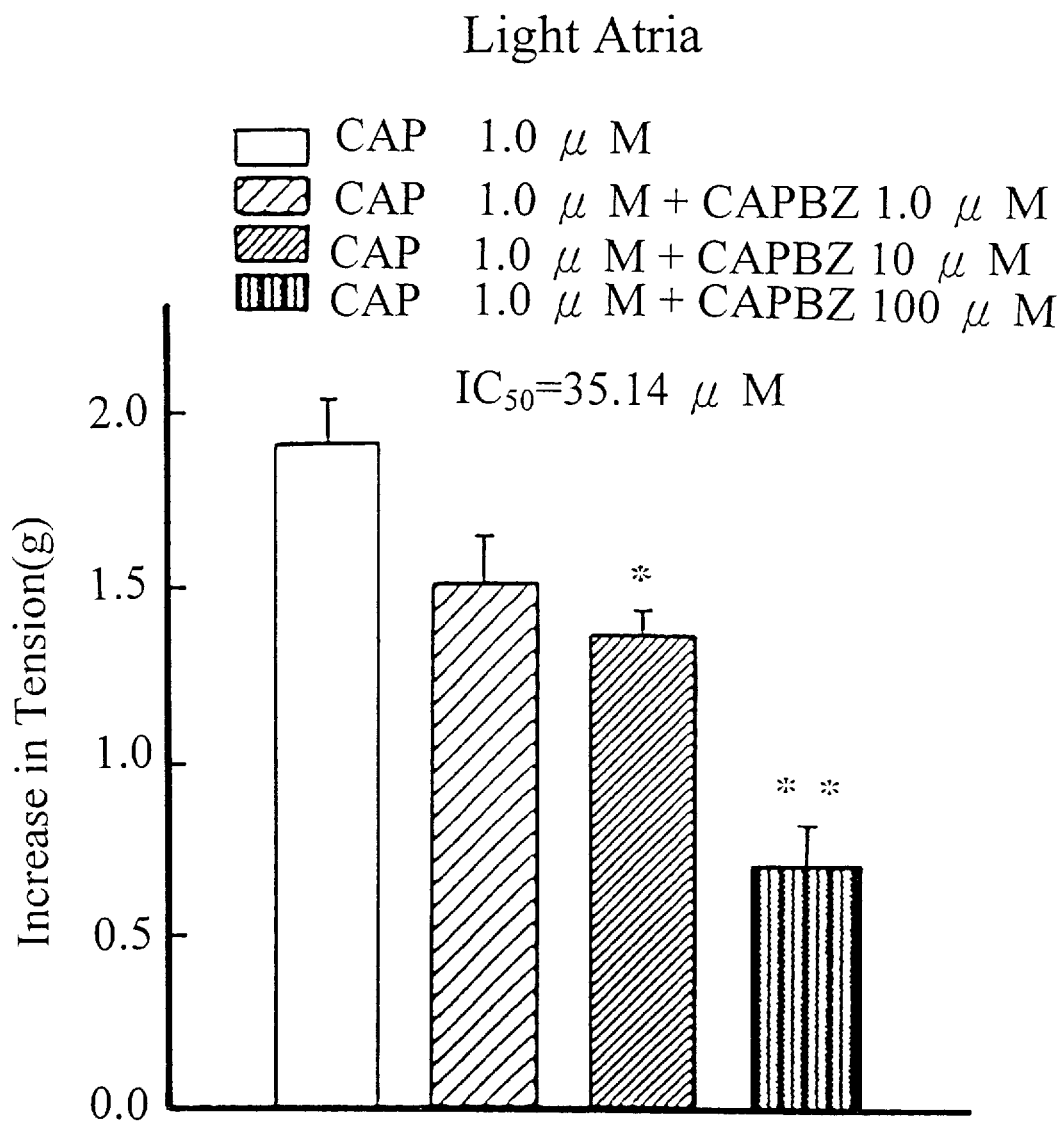

Cumulative addition of 0.01–30 μM capsaicin to the organ bath caused a concentration-dependent increase in contraction of isolated guinea-pig bronchi and trachea. These effects were shifted rightward in bronchi in the presence of compound 1 (CAPBZ, 1.0–100, μM)), compound 3 (CAPBI, 1.0–100 μM) and capsazepine (1–10 μM). This inhibitory effect of compound 1 and 3 were more effective in bronchi than in trachea (FIGS. 2A–C).

B. Antagonist activity of compound on capsaicin-induced contraction in the isolated guinea-pig atrium Also as shown in FIGS. 3A–3D, 1.0 μM capsaicin induced a positive inotropic and chronotropic effect in the isolated right and left guinea-pig atria, respectively. These effects were significantly inhibited in the presence of 0.1–10 μM compound 1 (CAPBZ), compound 6 (CAPCNC6), compound 11 (NVABI), compound 12 (NVADA), concentrationdependently. The $IC_{50}$ value against capsaicin-induced contractility for these compounds can be estimated from the data presented in FIGS. 3A–3D.

C. Antagonist activity of compound on capsaicin and substance Pinduced contractilities of isolated guinea-pig ileum The abdominal incisions for the guinea pig were made and ilea were isolated and placed in cold (4° C.) Tyrode's solution. 2.5 cm segments of ileum were then trimmed and suspended in an organ bath containing 20 ml low calcium Kreb's solution, aerated with 95% $O_2$ and 5% $CO_2$ at 37° C. As the method reported by M. Takaki et al. (Eur. J. Pharmacol. 174, 5762, 1989).

Figure 4A:
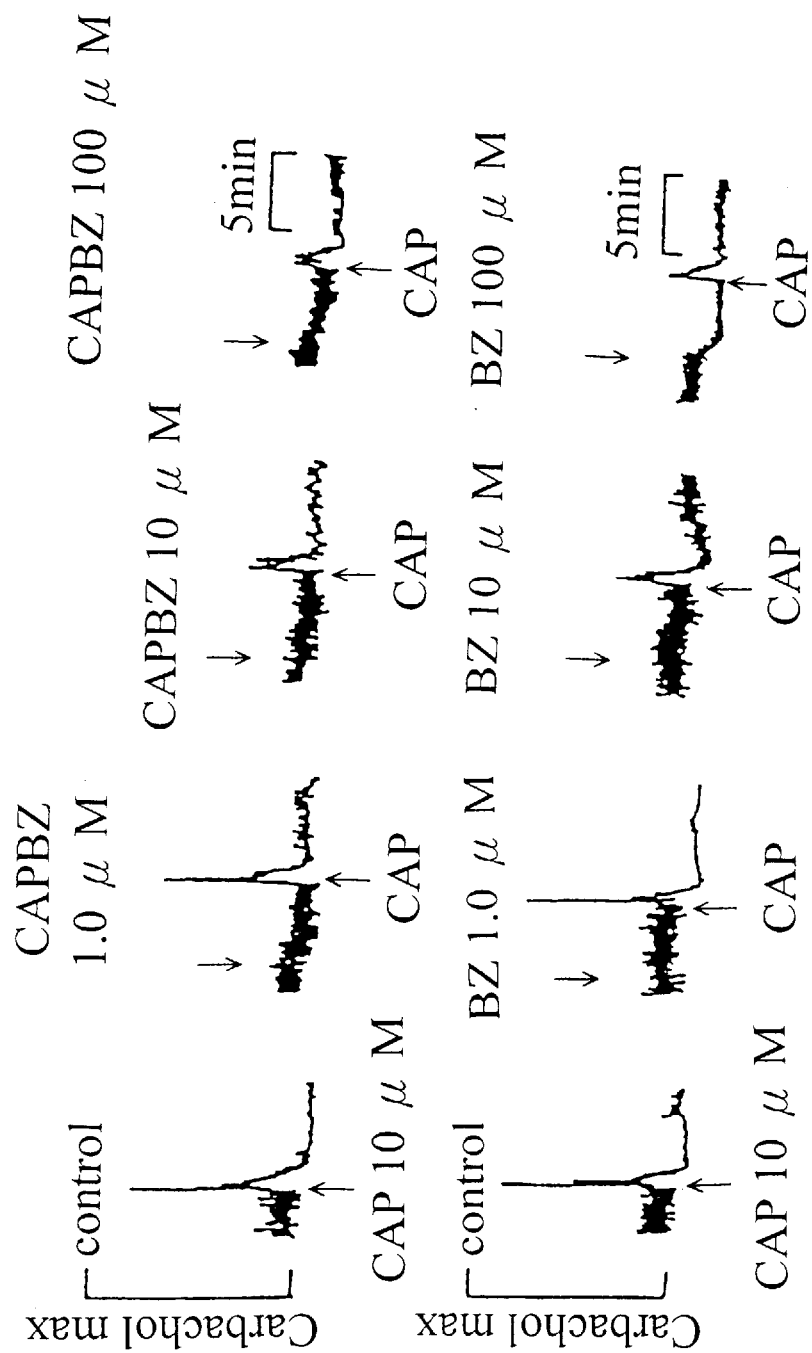
FIG. 4 The effects of CAPBZ on response of guinea-pig ileum to capsaicin (10 $\mu$M), substance P (SP, 0.1 $\mu$M), and carbachol (0.5 $\mu$M). Note concentration-dependently reduction of response to SP, and carbachol. Thirty minutes following washout, responses to SP, and carbachol were recovered.
Figure 4B:
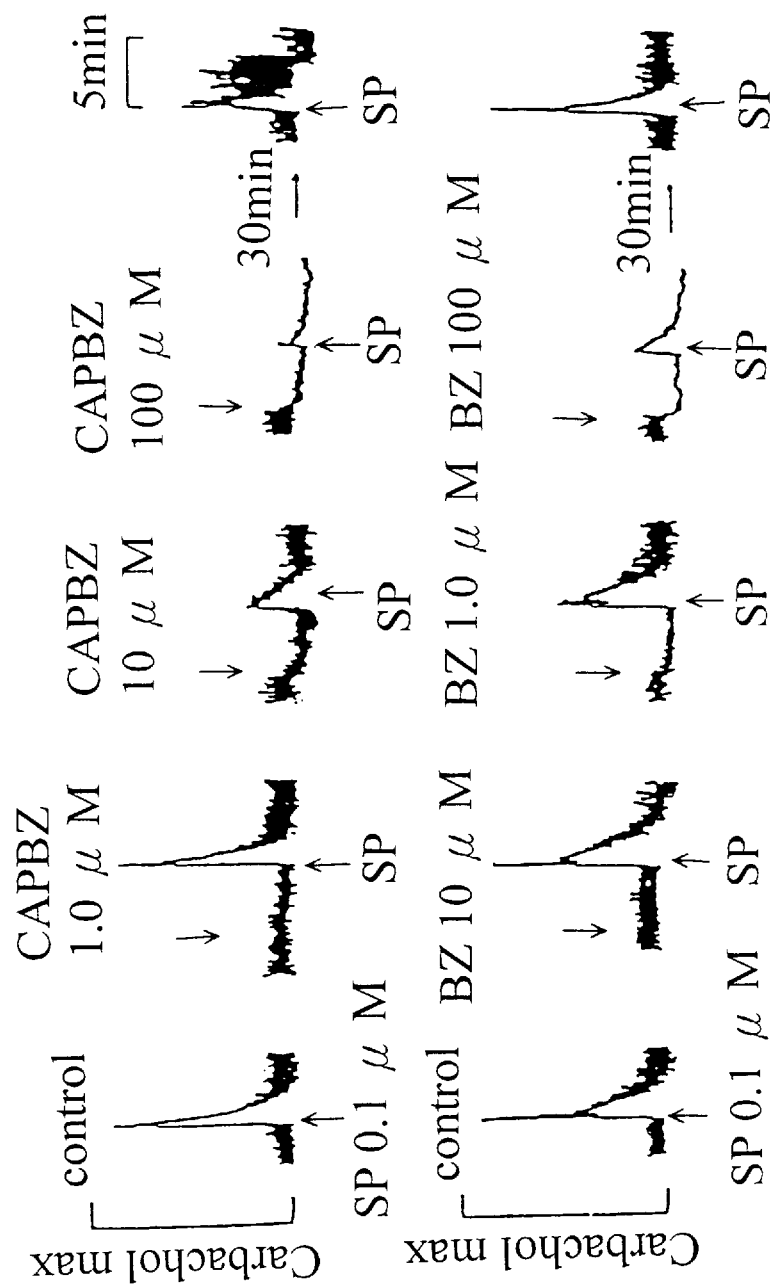
Figure 4C:
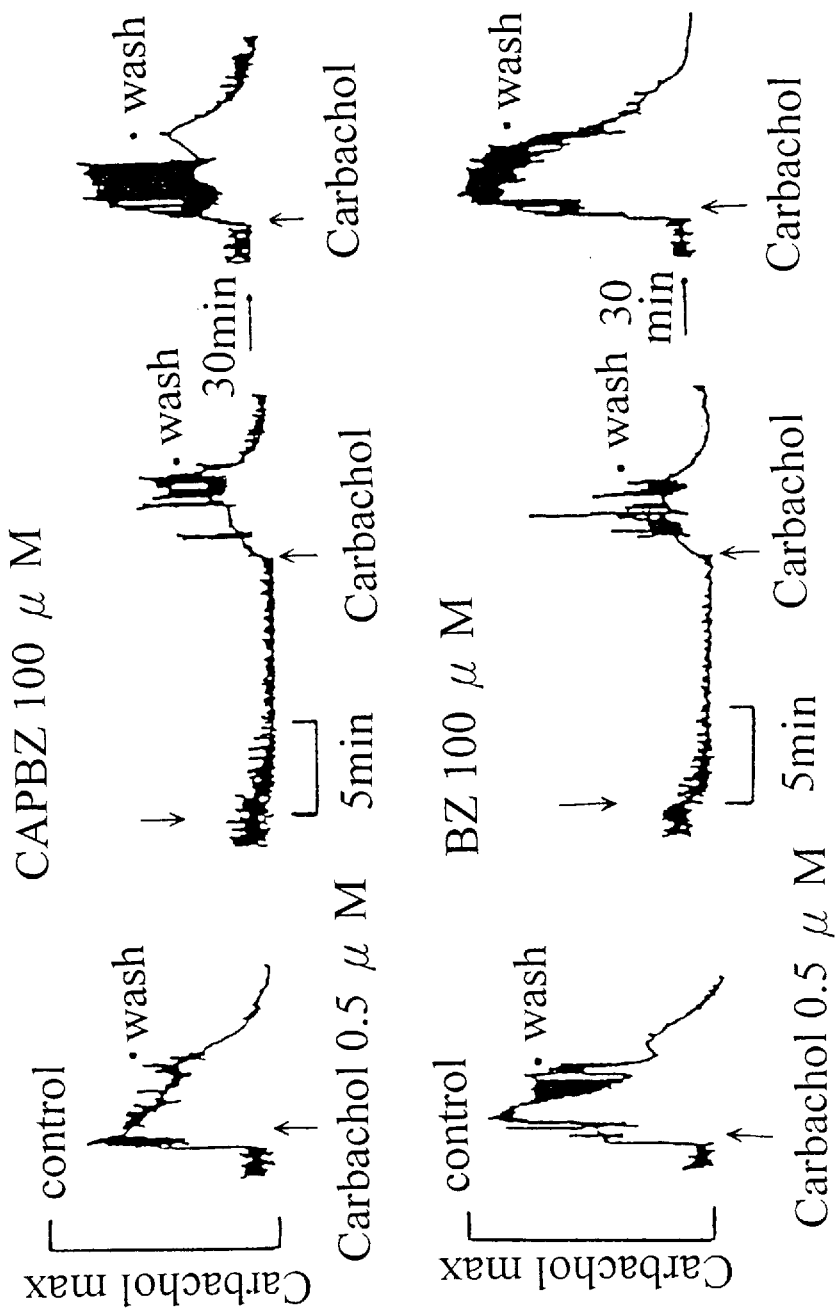

As shown in FIG. 4, carbachol was used as a control agent to induce maximum contraction of ileum smooth muscle; 10 μM capsaicin and 0.1 μM substance P (SP) induced weaker contractions. This effect of capsaicin or substance P was inhibited in the presence of 1.0–100 μM of compound 1 (CAPBZ), concentration-dependently.

D. Effects of compound on the calcium channel in the isolated guinea-pig atrium

Cumulative addition of $CaCl_2$ concentrations in the Kreb's solution could concentration-dependently produce a positive chronotropic effect in the isolated spontaneously beating right atrium, and a positive inotropic effect in the isolated electrically driven left guinea-pig atrium. Pretreatment with compound 1 and 6 could inhibit these calcium effects (FIGS. 5A–5B and FIGS. 6A–6B).

E. Ineffective effect on CGRP releasing in the isolated atrium

Figure 7:
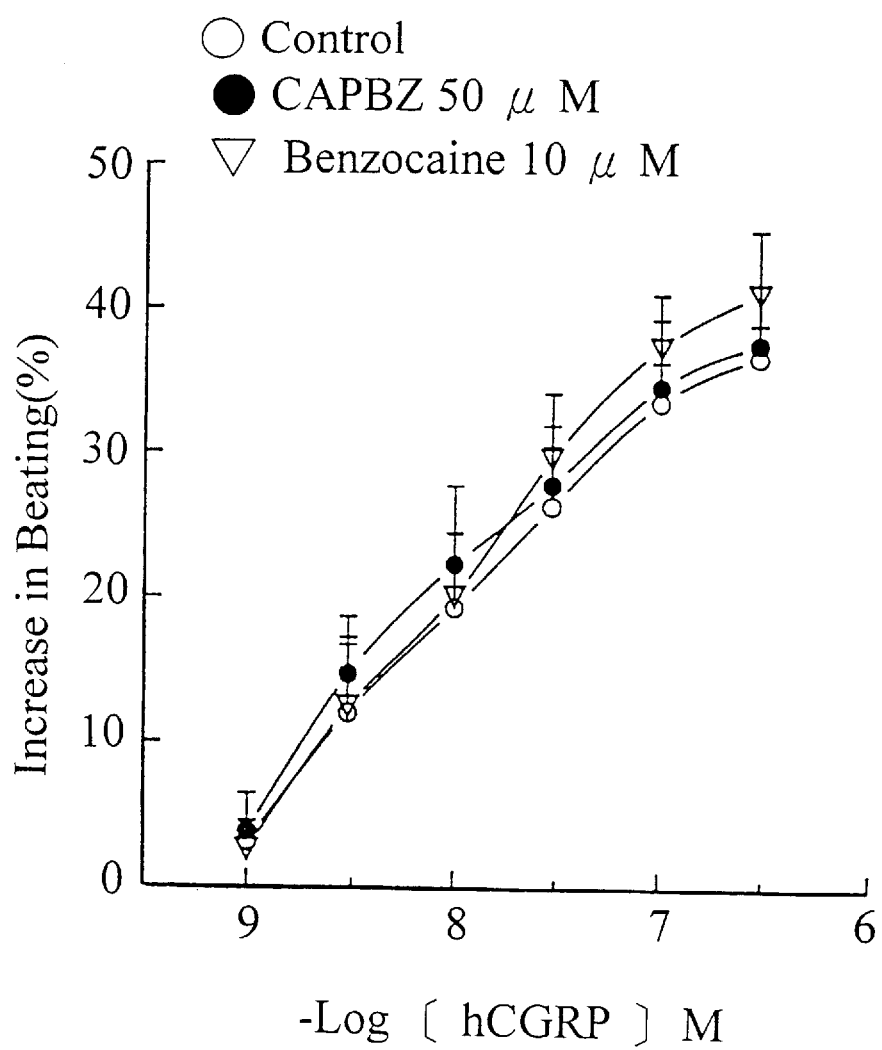
FIG. 7 Cumulative concentration-response curves for the chronotropic effects of hCGRP in the absence and presence of CAPBZ (50 $\mu$M) and benzocaine (10 $\mu$M) on spontaneous beatings of guinea-pig right atria. Each value is the mean±S.E.M. of six experiments.
Figure 8A:
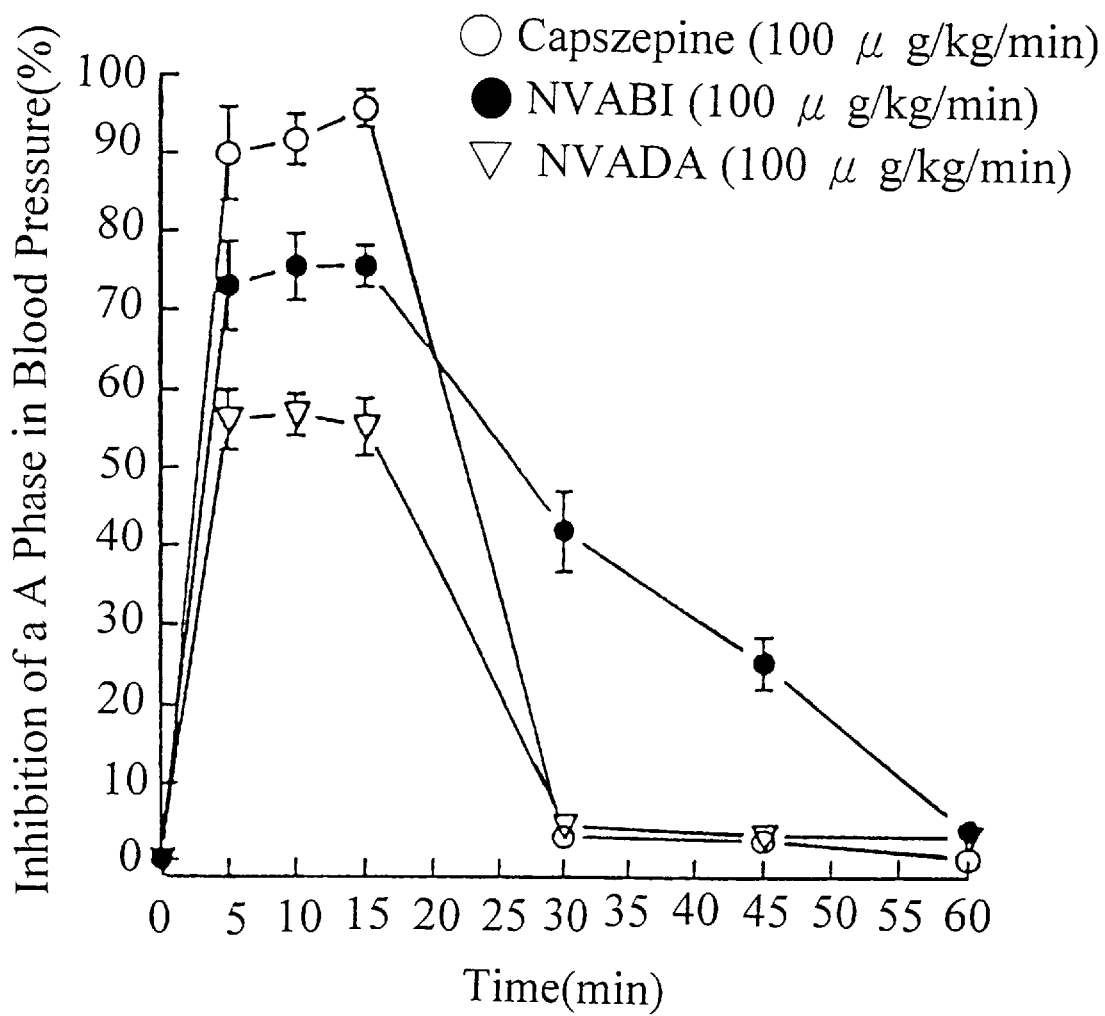
FIGS. 8A–8C Percentage of inhibition of capsaicin (10 $\mu$g/kg, i.v.) induced triphasic response during a 15 min infusion of capsazepine or NVABI or NVADA (100 $\mu$g/kg/min) and recovery from A, B and C phase of blood pressure after termination of each infusion. Each data was the mean±S.E.M. of six experiments.
Figure 8B:
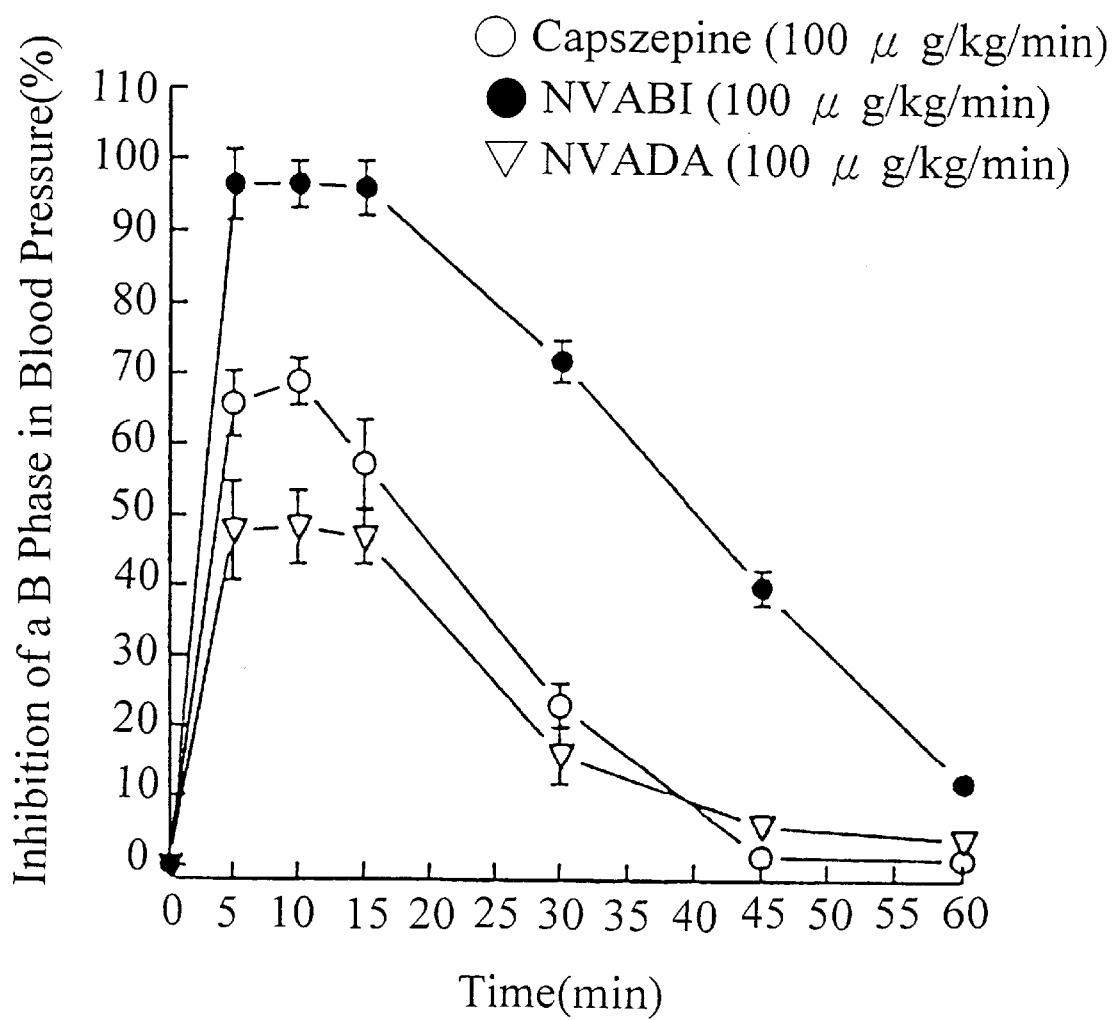
Figure 8C:
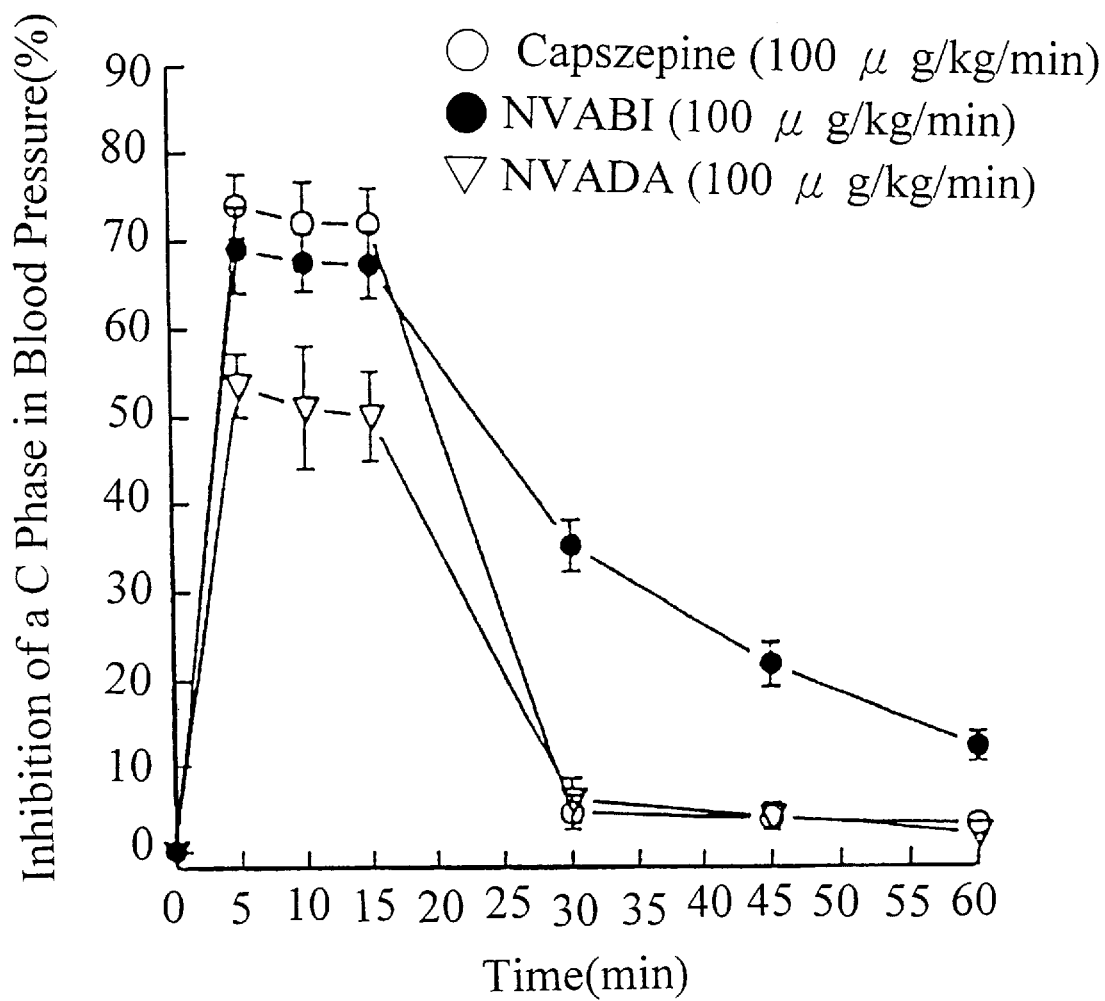

Cumulative addition of hCGRP to the organ bath concentrationdependently increased the beating in the right atrium and the tension in the electrically driven left atrium of the guinea pig. These effects were not inhibited by compound 1 (CAPBZ). After the pretreatment with CGRP for 30 minutes, compound 1 also could not change CGRP-induced contractilities (FIG. 7).

F. Effects of compounds on capsaicin-induced blood pressure and heart rate changes After 15 minutes, intravenous perfusion of NVABI, NVABZ, NVADA and capsazepine (100 μg/kg/min), bolus capsaicin (10 μg/kg, i.v.) was given at 5th, 10th, 15th, 30th, 45th and 60th minutes in the pentobarbital-anesthesized Wistar rats. This experiment was carried out to study the antagonistic effects of these compounds on capsaicin elicit triphasic response of blood pressure. The results indicated the antagonist activities of NVABI, NVABZ, and capsazepine were recovered to basal level by saline infusion for 30, 45, and 60 minutes gradually. Estimated recovery half life of capsaicin-induced blood pressure changes (A, B, and C effect) for NVABI was 10.67, 4.30, and 21.75 min, for NVABZ 55.13 min, for NVADA 4.30, 9.01, and 4.49, and for capsazepine 2.73, 2.89, and 3.78 min (Table 1 & 2). The duration order of their antagonist activities was NVABZ>NVABI>capsazepine. The efficacy order of their antagonist activities was capsazepine>NVABZ>NVABI in the A effect, NVABI>capsazepine>NVABZ in the B effect, and capsazepine>NVABI>NVABZ in the C effect. These compounds could not inhibit calcitonin gene-related peptide, substance P, and bradykinininduced hypotensive effects. Intrathecal perfusion of these compounds also reversed epigastric intraarterial capsaicin (10 μg/kg)-induced hypotensive reflex in rats (Table 3). It is concluded that NVABI, NVABZ, NVADA, and capsazepine all modulate the presynaptic capsaicin-sensitive sensory neurons and thus may inhibit capsaicin-induced release of neuropeptides, but are different from each other in their pharmacokinetic properties.

III. Pharmaceutical Compositions

The novel compounds of this invention together with a conventional adjuvant, carrier, or diluent, and if desired in the form of pharmaceutically acceptable salts, may be prepared in the form of pharmaceutical compositions and unit dosages. In such forms, they may be employed as solids, or liquids, for oral use; in the form of suppositories for rectal administration; in the form of sterile injectable solutions for parental (including subcutaneous) use.

The solid pharmaceutical dosages may comprise disintegrating agents such as starch, sodium carboxymethylcellulose, and/or binders such as ethyl alcohol, glycerin, and/or carriers such as magnesium stearate, lactose, which are prepared by conventional pharmaceutical methods. The sterile injectable solutions, dosages, or other liquid preparations can be adjusted with buffers, such as phosphate solutions, if desired, with auxiliary agents, emulsifiers, which particularly comprise aqueous solutions or salt solutions of the novel compounds. The novel pharmaceutical compositions and unit dosages thereof allow the formation of a pharmaceutically acceptable salt, are extremely useful in selectively antagonizing capsaicin-sensitive sensory neurons, inhibiting innervation of the atrium, airway and ileum smooth muscles in vitro, and as well as producing direct cardioinhibitory effects, tachyphylaxis. The novel compounds of the invention may accordingly be administered to a subject, e.g. a living animal body, including a human, and should be adjusted according to the complexity of the symptoms.

IV. Synthesis and its Scheme

EXAMPLE 1

N[P-(carboxylic acid ethyl ester) phenylamine-(4-oxymethylene, 5-methylene)-3-methoxybenzyl] nonanamide, capsazocaine, (compound 1)

10 g nonivamide was dissolved in a mixture of absolute methanol 20 ml, mixed with 5.7 g benzocaine in 10 ml absolute methanol solution, then poured into a three-neck flask, adding 10 ml 34–37% formaldehyde solution, 5 ml acetic acid, then refluxing under 70°–75° C. for 24 hrs. After cooling, the solvent was evaporated. The residue was recrystallized from ethylacetate to give compound 1, Yield 77%.

EXAMPLE 2

N[Ethylamino-(4-oxymethylene 5-methylene)-3-methyoxybenzyl] nonanamide (compound 2)

10 g nonivamide was dissolved in 1000 ml ethanol, added to 3.5 mole times ethylamine, 4 mole times formaldehyde, and drops of acetic acid, then refluxed under room temperature for 24 hrs. After cooling, the solvent was evaporated. The residue was recrystallized from n-hexane to give compound 2.

EXAMPLE 3

N-hexylamino-(4-oxymethene, 5-methylene)-3-methoxybenzyl] nonanamide (compound 6)

10 g nonivamide and 5 ml hexylamine was used as the starting material and treated according to the procedure described in example 1 to give compound 6.

EXAMPLES 4–12

The compounds 3–5, 7–12 can be prepared in a manner analogous to those described in example 1–3. The physical constants and spectral data are shown in Section IV.

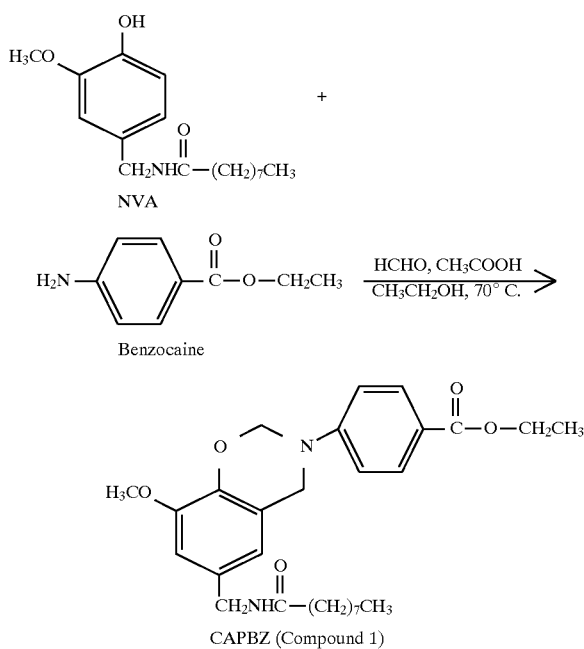

Scheme 1:

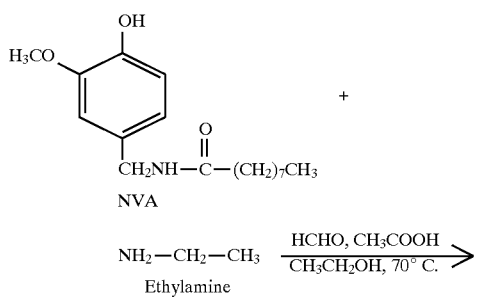

Scheme 2:

7
-continued

Scheme 2:

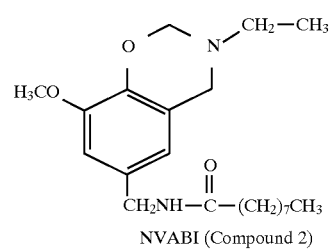

NVABI (Compound 2)

Scheme 3:

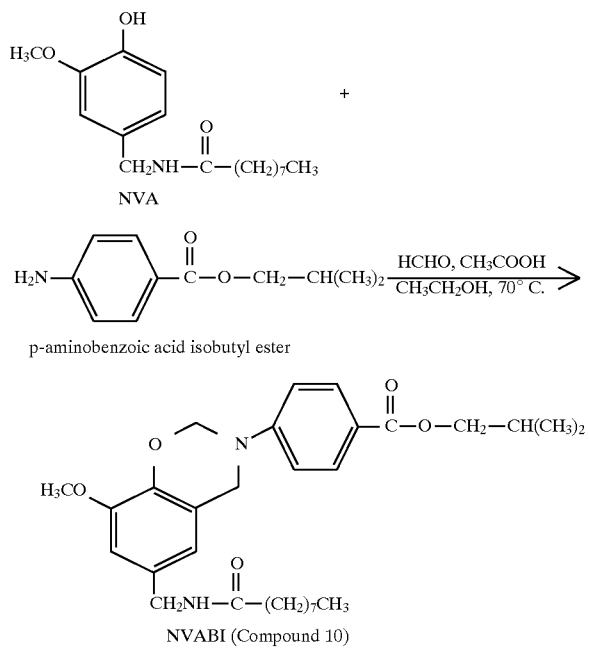

NVABI (Compound 10)

Scheme 4:

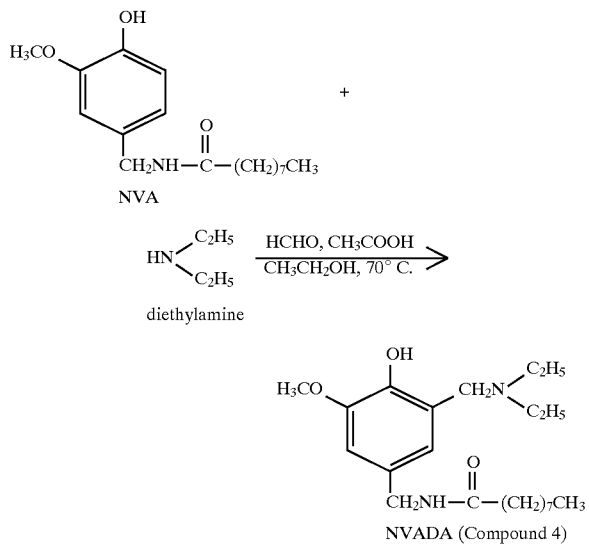

NVADA (Compound 4)

8

V. Pharmaceutical Formulation

A typical tablet which may be prepared by conventional tabletting techniques contains

| | |
|---|---|
| active compound | 40 mg |
| lactose | 30 mg |
| starch | 8 mg |
| mag.stearate | 10 mg |
| corn starch | 12 mg |

VI. Physical Constants and Spectral Data of Synthesized Examples

The physical constants and spectral data are shown as follows:

Compound 1

N[P-(carboxylic acid ethyl ester)-phenylamine-(4-oxymethylene, 5-methylene)-3-methoxybenzyl] nonanamide, capsazocaine, (compound 1)

mp: 145°–147.5° C.,

1H-NMR(CDCl$_3$):

δ 0.87 (t, 3H, CH$_3$), 1.32–2.20 (m, —(CH$_2$)×7), 3.84 (s, 3H, OCH$_3$), 4.32 (q, 2H, —COO—CH$_2$CH$_3$), 4.32 (d, 2H, ArCH$_2$—NHCO—), 4.65 (S, 2H, ArCH$_2$—N═), 5.45 (S, 2H, ArOCH$_2$═N—), 5.71 (m, 1H, NH), 6.57 (d, 1H, Ar), 6.66 (d, 1H, Ar), 7.08 (m, 2H, Ar—COO—), 7.94 (m, 2H, Ar—N);

IR(KBr) υ (cm$^{-1}$)

1650 cm$^{-1}$ (C═O), 1720 cm$^{-1}$ (—COOR)

Figure 5A:
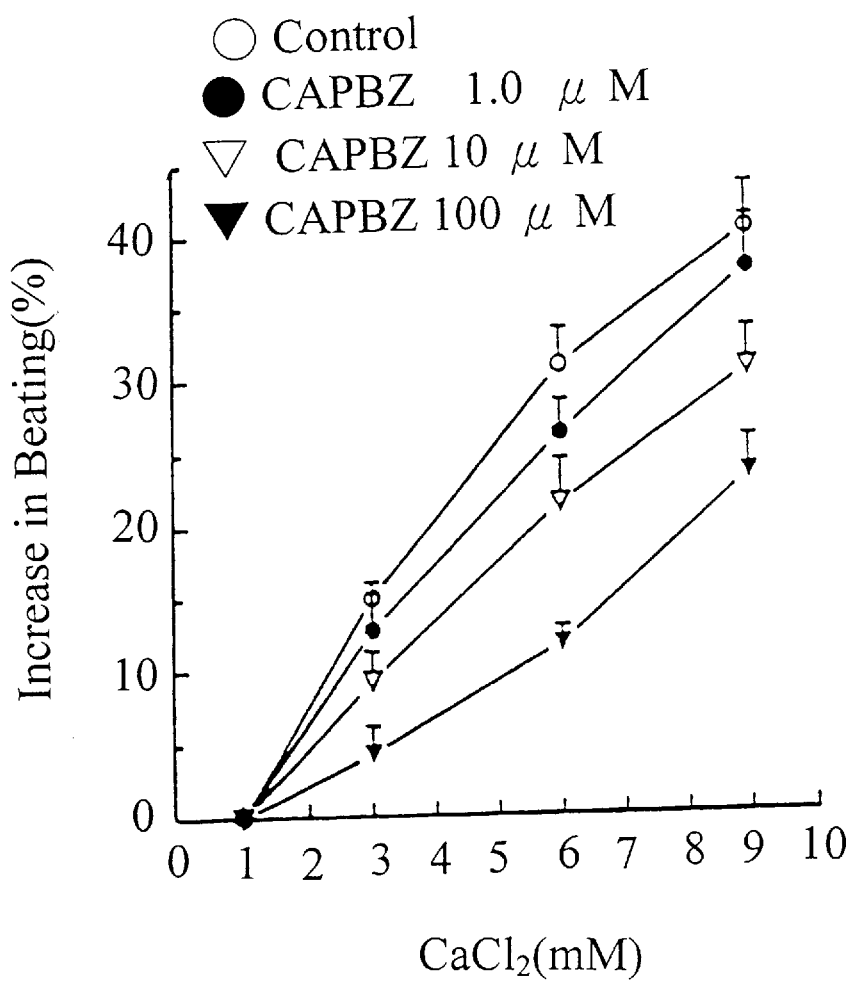
FIGS. 5A–5B Effect of CAPBZ on the positive chronotropic effects of increasing $CaCl_2$ concentrations in the isolated guinea-pig right atria and electrically-driven guinea-pig left atria. Each point represents the mean of six experiments; vertical bars represent the S.E.M.
Figure 5B:
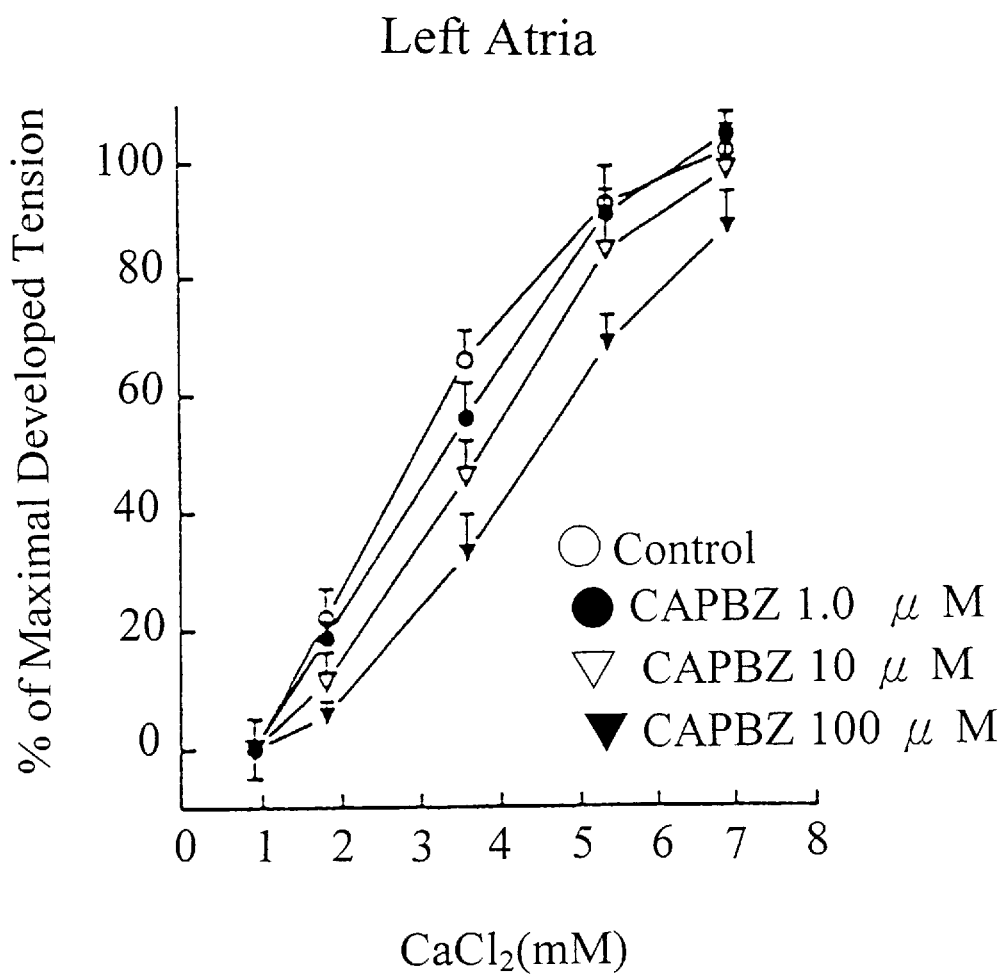
Figure 6A:
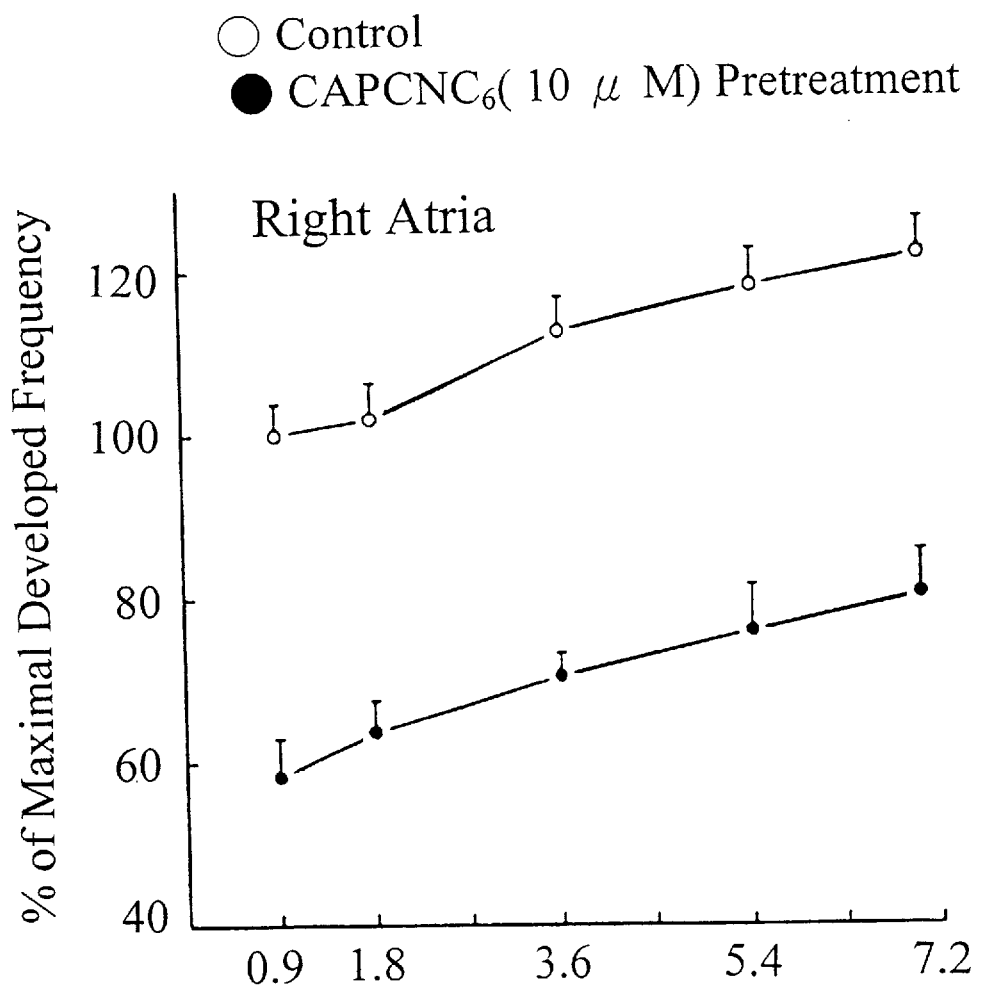
FIGS. 6A–6B Effect of CAPCNC6 (10 $\mu$M) on the positive chronotropic (spontaneously beating right atrium) and inotropic (electrically-driven left atria) effect of increasing $Ca^{2+}$ concentrations in guinea pigs. Beating rate and tension were expressed as % of control values. Data represents the mean±S.E.M. (n=7).
Figure 6B:
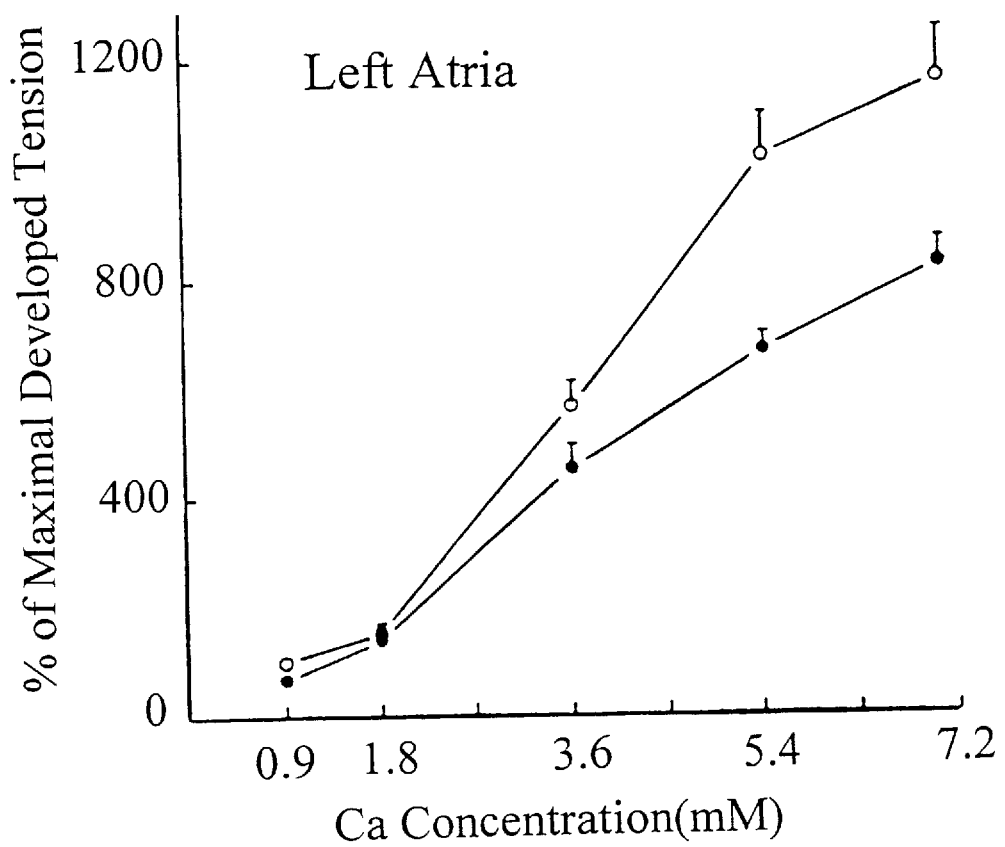

3300 cm$^{-1}$ (NH—CO—);

MS(FAB+):MS m/z 483(M+H)+ (FIGS. 5A–5B);

Anal. Calcd for C$_{28}$H$_{38}$N$_2$O$_5$;

C, 69.57%, H, 7.88%, N, 5.80%, O, 16.75%,

Found:

C, 69.53%, H, 7.90%, N, 5.75%, O, 6.82%,

UV(EtOH) λ max nm (log ε): (FIGS. 6A–6B) 211 (2.45), 289 (2.36)

Compound 2

N[Ethylamino-(4-oxymethylene, 5-methylene)-3-methyoxybenzyl] nonanamide (compound 2)

mp: 94°–97° C.

$^1$H-NMR; (CDCl$_3$) (FIGS. 3A–3D):

δ 0.87 (t, 3H, CH$_3$), 1.3–1.61 (m, CH$_2$), 2.21 (t, 2H, J=7.58, NH—CO—CH$_2$), 2.83 (tert, 2H, J=10.71, N—CH$_2$), 3.85 (s, 3H, OCH$_3$), 3.98 (s, 2H, Ar—CH$_2$), 4.32 (d, 2H, J=2.84, Ar—CH$_2$—N), 4.95 (s, 2H,O—CH$_2$—N), 5.63 (s, 1H, NH), 6.65–6.66 (d, 2H, Ar—H);

IR(KBr) υ (cm$^{-1}$)

1650 cm$^{-1}$ (C═O), 3300 cm$^{-1}$ (NH) (FIG. 4);
V (EtOH) λ max nm (log ε):
7.33
(FAB-MS) M/Z: 362 (FIGS. 6A–6B)
Compound 3
[N-Allylamino-(4-oxymethylene, 5-methylene)-3-methoxybenzyl] nonanamide
1H-NMR (CDCl$_3$):
δ0.87 (t, 3H, CH$_3$),
1.2–2.25 (m, 14H, 7×CH$_2$),
3.40 (d, 2H, =NCH$_2$),
3.86 (s, 3H, OCH$_3$),
3.98 (s, 2H, ArCH$_2$N=),
4.32 (d, 2H, ArCH$_2$NHCO),
4.94 (s, 2H, OCH$_2$N=),
5.15–5.28 (m, 1H, C=CH—),
5.63 (b, 1H, NH),
5.80–5.95 (m, 1H, H—C=C),
6.48 (d, 1H, Ar—H),
6.67 (d, 1H, Ar—H).
Compound 4
[N-diethylamino-(4-oxymethylene, 5-methylene)-3-methoxy, benzyl] nonanamide
1H-NMR (CDCl$_3$):
δ 0.8–0.9 (t, 3H, CH$_3$),
0.98–1.05 (t, 3H, CH$_3$),
1.10–1.20 (t, 3H, CH$_3$),
1.20–2.17 (m, 14H, 7×CH$_2$),
2.48–2.60 (q, 2H, =NCH$_2$),
2.79–2.91 (q, 2H, =NCH$_2$),
3.67 (s, 2H, Ar—CH$_2$N),
3.72 (s, 3H, OCH$_3$),
4.12 (d, 2H, ArCH$_2$NHCO),
6.54 (s, 1H, Ar—H),
6.73 (s, 1H, Ar—H),
8.24 (b, 1H, NH).
Compound 5
[N-tetramethyleneamino-(4-oxymethylene, 5-methylene)-3-methoxybenzyl] nonanamide
[M+]: 376
1H-NMR (CDCl$_3$):
δ 0.8–0.9 (t, 3H, CH$_3$),
1.15–2.60 (m, 22H, 11×CH$_2$),
3.68 (s, 2H, Ar—CH$_2$N),
3.72 (s, 3H, OCH$_3$),
4.13 (d, 2H, ArCH$_2$NHCO),
6.55 (s, 1H, Ar—H),
6.73 (s, 1H, Ar—H),
8.16 (b, 1H, NH).
Compound 6
N-[hexylamino-(4-oxymethene, 5-methylene)-3-methoxybenzyl] nonanamide (compound 6)
mp: 107.5°–108.5° C.,
1H-NMR(CDCl$_3$):
δ 0.87 (t, 6H, CH$_3$),
1.28 (s, 16H, CH$_2$),
1.60 (m, 4H, CH$_2$),
2.21 (t, 2H, J=7.51 Hz, CO—CH), 2.74 (t, 2H, J=7.35 Hz, N—CH$_2$),
3.85 (s, 3H, OCH$_3$),
3.96 (s, 2H, Ar—CH$_2$—NH),
4.32 (d, 2H, J=5.68 Hz, Ar—CH$_2$—NH),
4.93 (s, 2H, O—CH$_2$—N),
5.72 (t, 1H, NH),
6.49 (d, 1H, J=1.64 Hz, Aromatic-H),
6.65 (d, 1H, J=1.44 Hz, Aromatic-H)
$^{13}$C-NMR(CDCl$_3$):
δ 14.1 (CH$_3$),
22.6, 25.8, 26.9, 28.1, 29.2, 29.3, 31.7 & 31.8 (aliphatic CH$_2$),
36.9 (CO—CH$_2$),
43.5 (Ar—CH$_2$—NH),
50.0 (Ar—CH$_2$—NH)
51.5 (N—CH$_2$),
55.9 (OCH$_3$),
82.9 (O—CH$_2$—N),
109.2, 118.7, 120.7, 130.0, 143.0 & 147.8 (Ar—C)
172.9 (C=O)
IR (HBr) υ max:
3300 cm$^{-1}$(N—H)
2920 & 2840 cm$^{-1}$ (CH$_2$)
1640 cm$^{-1}$ (C—O)
1540, 1490, 1220, 1150 & 920 cm$^{-1}$
UV (C$_2$H$_5$OH) λ max (log ε):
285 (3.346), 216 (4.335) nm
Anal. Calcd for C$_{25}$H$_{42}$O$_3$N$_2$
N 6.65%; C 71.28%; H 10.07%
MS (FAB+):
M/Z 419 (M+H)+ 418
MSHRFAB 418.3278
Compound 7
[p-acetic acid ethylester-benzylamino-(4-oxymethylene, 5-methylene)-3-methoxybenzyl] nonanamide
1H-NMR (CDCl$_3$):
0.83–0.90 (t, 3H, CH$_3$)
1.03–2.22 (s, 14H, CH$_2$×7)
3.51 (s, 2H, ArCH$_2$COOC$_2$H$_5$)
3.83 (s, 3H, OCH$_3$)
4.06–4.18 (q, 2H, COOCH$_2$CH$_3$)
4.29–4.32 (d, 2H, ArCH$_2$NHCO)
4.58 (s, 2H, ArCH$_2$N=)
5.41 (s, 2H, ArOCH$_2$N=)
5.62 (b, 1H, NH)
6.52 (d, 1H, ArH)
6.63 (d, 1H, ArH)
7.05–7.20 (m, 4H, 4×ArH)
Compound 8
[p-carboxylyl acid-benzylamino-(4-oxymethylene, 5-methylene)-3-methoxybenzyl] nonanamide
1H-NMR (CDCl$_3$):
0.81–0.87 (t, 3H, CH$_3$)
1.23–2.14 (m, 14H, CH$_2$×7)
3.69 (s, 3H, OCH$_3$)
4.13–4.15 (d, 2H, ArCH$_2$NHCO)
4.69 (s, 2H, ArCH$_2$N=)

5.48 (s, 2H, ArOCH$_2$N=)
6.58–6.70 (q, 2H, ArH)
7.16–7.20 (d, 2H, ArCOO)
7.78–7.82 (d, 2H, ArCOO)
8.14–8.19 (t, 1H, CH$_2$NHCO)
12.44 (s, 1H, ArCOOH).
Compound 9
N[o-(carboxylic acid methylester)-phenylamino-(4-oxymethylene, 5-methylene)-3-methoxybenzyl] nonamide
1H-NMR (CDCl$_3$):
0.87 (t, 3H, CH$_3$)
1.10–2.20 (m, 14H, CH$_2$×7)
3.73 (s, 3H, COOCH$_3$)
3.84–3.87 (d, 3H, OCH$_3$)
4.30 (d, 2H, ArCH$_2$NHCO)
4.42 (s, 2H, ArCH$_2$N=)
5.70 (b 1H, NH)
6.74 (m, 2H, 2×ArH)
7.08–7.10 (d, 1H, ArH)
7.13–7.14 (d, 12H, ArH)
7.74–7.75 (d, 2H, ArH)
Compound 10
N[p-carboxylic acid isobutylester-phenylamino-(4-oxymethylene, 5-methylene)-3-methoxybenzyl] nonamide
mp: 110–110.5 C.
1H-NMR (CDCl$_3$):
δ 0.87 (t, 3H, CH$_3$)
δ 1.27 (m, 12H, (CH$_2$)6 CH$_3$)
δ 2.18 (d, 2H, —CO—CH$_2$—, J=8.2 Hz)
δ 3.84 (s, 3H, OCH$_3$)
δ 4.05 (d, 2H, COOCH$_2$CH$_3$, J=6.6 Hz)
δ 4.34 (d, 2H, —ArCH$_2$NH—, J=5.7 Hz)
δ 4.67 (s, 1H, N—H)
δ 6.62 (d, 1H, Ar—H, J=3.4 Hz)
δ 7.09 (d, 2H, Ar—H—COO—, J=9.1 Hz)
δ 7.96 (d, 2H, ArH, J=9.0 Hz)
IR (KBr) (cm$^{-1}$)
1650 (CO)
1720 (COOR)
3300 (NH)
MS(FAB+): MS m/z 510 (M+H)
Anal. Calcd. for C$_{30}$H$_{42}$N$_2$O$_5$
Found:
  C, 70.18%, H, 8.25%, N, 5.65%
Compound 11
N-[(4-hydroxy, 5-diethylaminomethyl)-3-methyoxybenzyl] nonamide
mp: 218–218.5 C.
1H-NMR (CDCl$_3$)
δ 0.87 (t, 3H, CH$_3$, J=6.2 Hz)
δ 1.24 (m, 12H, (CH$_2$)$_6$CH$_3$)
δ 2.12 (t, 2H, —NHCOCH$_2$—, J=7.3 Hz)
δ 2.83 (m, 2H, NCH$_2$—)
δ 3.72 (s, 3H, OCH$_3$)
δ 4.14 (d, 2H, Ar—CH$_2$—, J=5.8 Hz)
δ 6.54 (d, 1H, Ar—H, J=1.7 Hz)
IR(KBr) (cm$^{-1}$)
1650 cm$^{-1}$ (CO)
2950 cm$^{-1}$ (CH)
MS (FAB+):MS m/z 378 (M+H)+
Anal. Calcd for C$_{22}$H$_{38}$N$_2$O$_3$
Compound 12
N[p-ethylketone-phenylamino-(4-oxymethylene, 5-methylene)-3-methoxybenzyl] nonamide
Melting point: 124°–126° C.
NMR
δ 0.87 (3H, t, CH$_3$—(CH$_2$)$_7$—)
1.256 (3H, t, CH$_3$—CH$_2$CO—)
1.25–1.33 (12H, m, 6×(CH$_2$)$_6$)
2.20 (2H, t, CO—CH$_2$—)
2.92 (2H, q, CH$_3$CH$_2$CO)
3.85 (3H, s, OCH$_3$)
4.68, 5.47 (each 2H, s, —CH$_2$—N—CH$_2$—O—)
5.65 (1H, t, —CH$_2$—NHCO—)
6.58 (1H, s, 3—H)
6.67 (1H, s, 5—H)
7.10 (2H, d, 2' and 6'—H)
7.91 (2H, d, 3'and 5'—H)

TABLE 1

Recovery half-life of capsaicin-induced blood pressure (A, B and C phase) changes during a 15 min infusion of NVABI, NVADA or capsazepine

| | $t_{1/2}$ (min.)* | | |
|---|---|---|---|
| Compd. | A phase | B phase | C phase |
| NVABI | 10.67 | 15.75 | 21.75 |
| NVADA | 4.30 | 9.00 | 4.49 |
| Capsazepine | 2.73 | 2.89 | 3.78 |

*$t_{1/2}$ was calculated by one compartment model.

TABLE 2

Recovery half-life of capsaicin-induced heart rate changes (fast and slow phase) during a 15 min infusion of NVABI, NVADA or capsazepine.

| | $t_{1/2}$ (min)* | |
|---|---|---|
| Compd. | Fast phase | Slow phase |
| NVABI | 11.95 | 15.75 |
| NVADA | 5.33 | 6.00 |
| Capsazepine | 1.36 | 3/52 |

*$t_{1/2}$ was calculated by one compartment model.

TABLE 3

Effects of intrathecal infusion (i.t.) of 1 nmole of NVABI, NVADA or capsazepine on the depressor reflex responses to intraarterial injection of capsaicin (10 μg/kg) induced blood pressure changes.

| Pretreatment (i.t. 1 nmole) | Capsaicin (i.a., 10 μg/kg) |
|---|---|
| None | −19.6 ± 1.9 |
| NVABI | 19.2 ± 2.5* |
| NVADA | −10.6 ± 2.5 |
| Capsazepine | 25.8 ± 3.0* |

All values after pretreatment differ significantly (* $P<0.05$) from control. Each datum represents the mean±S.E.M. (n=6)

What we claim is:
1. A capsaicin derivative having the formula

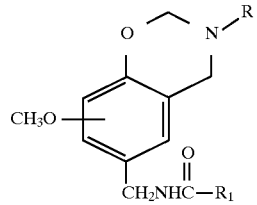

wherein R is a member selected from the group consisting of —R$_1$

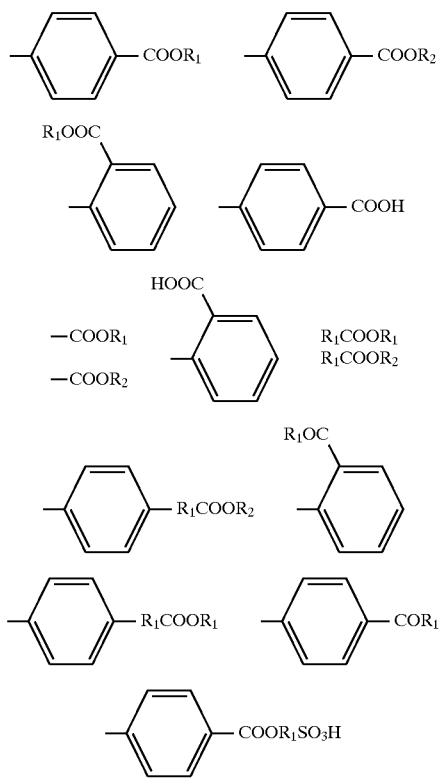

wherein R$_1$ is a member selected from the group consisting of C$_{1-12}$ alkyl, C$_{1-12}$ alkenyl, C$_{1-12}$ alkylene, and C$_{1-12}$ alkenylene, and wherein R$_2$ is a member selected from the group consisting of H, C$_{1-3}$ alkylene-NR$_1$R$_1$, and C$_{1-6}$ alkenylene-NR$_1$R$_1$.

2. The capsaicin derivative as defined in claim 1 wherein R$_1$ is selected from the group consisting of C$_{1-8}$ alkyl, C$_{1-8}$ alkenyl, C$_{1-8}$ alkylene, and C$_{1-8}$ alkenylene, and wherein R$_2$ is selected from the group consisting of H, C$_{1-3}$ alkylene-NR$_1$R$_1$, and C$_{1-3}$ alkenylene-NR$_1$R$_1$.

3. The capsaicin derivative as defined in claim 1 wherein R$_1$ is selected from the group consisting of C$_{1-6}$ alkyl, C$_{1-6}$ alkenyl, C$_{1-6}$ alkylene, and C$_{1-6}$ alkenylene.

4. The compound as defined in claim 1 wherein R$_1$ and R$_2$ are straight-chained or branched.

5. A pharmaceutical salt prepared from the compound as defined in claim 1.

6. A pharmaceutical composition comprising a compound having the following formula

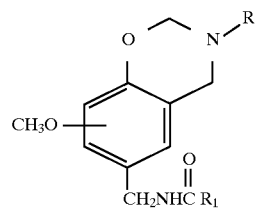

wherein R is selected from the group consisting of —R$_1$

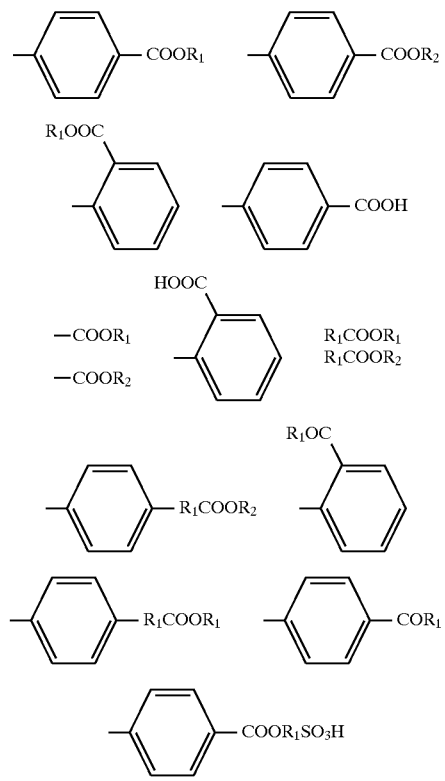

wherein R$_1$ is selected from the group consisting of C$_{1-12}$ alkyl, C$_{1-12}$ alkenyl, C$_{1-12}$ alkylene, and C$_{1-12}$ alkenylene, and wherein R$_2$ is selected from the group consisting of H, C$_{1-6}$ alkylene-NR$_1$R$_1$ and C$_{1-6}$ alkenylene-NR$_1$R$_1$, and wherein said composition contains an amount of said compound sufficient to selectively antagonize capsaicin-sensitive sensory neurons of a living animal body.

7. A pharmaceutical composition comprising a compound having the following formula

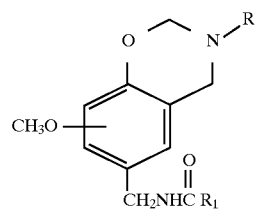

wherein R is selected from the group consisting of —$R_1$

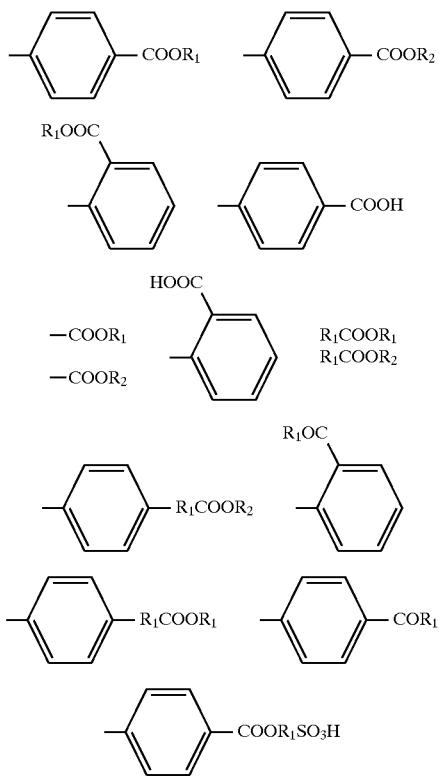

wherein $R_1$ is selected from the group consisting of $C_{1-12}$ alkyl, $C_{1-12}$ alkenyl, $C_{1-12}$ alkylene, and $C_{1-12}$ alkenylene, and wherein $R_2$ is selected from the group consisting of H, $C_{1-6}$ alkylene-$N_1R_1$, and $C_{1-6}$ alkylene-$NR_1R_1$, and wherein said composition contains an amount of said compound sufficient to inhibit innervation of an airway in a living animal body.

8. A pharmaceutical composition comprising a compound having the following formula

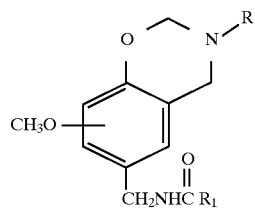

wherein R is selected from the group consisting of —$R_1$

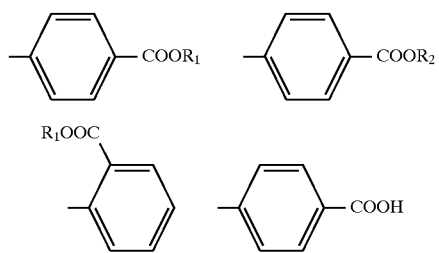

-continued

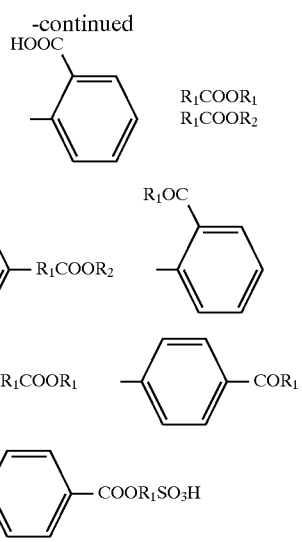

wherein $R_1$ is selected from the group consisting of $C_{1-12}$ alkyl, $C_{1-12}$ alkenyl, $C_{1-12}$ alkylene, and $C_{1-12}$ alkenylene, and wherein $R_2$ is selected from the group consisting of H, $C_{1-6}$ alkylene-$NR_1R_1$, and $C_{1-6}$ alkylene-$NR_1R_1$, and wherein said composition contains an amount of said compound sufficient to inhibit innervation of the ileum smooth muscles of a living animal body.

9. A pharmaceutical composition comprising a compound having the following formula

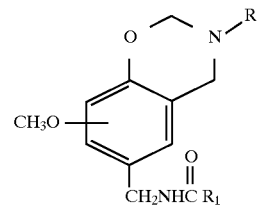

wherein R is selected from the group consisting of —$R_1$

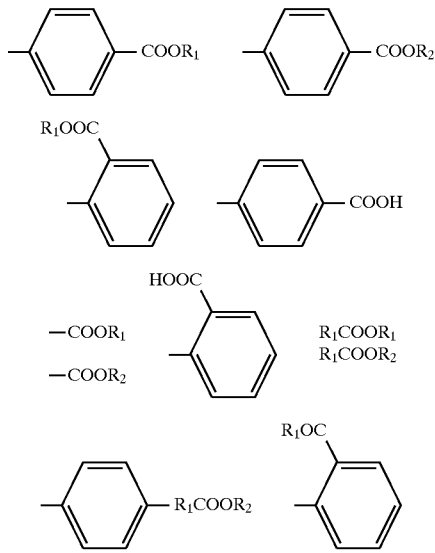

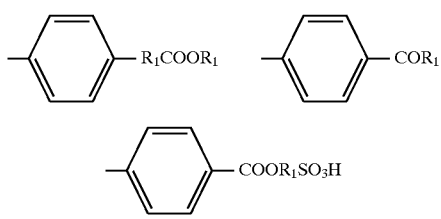

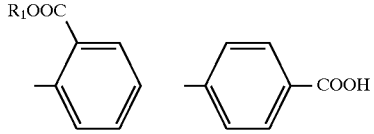

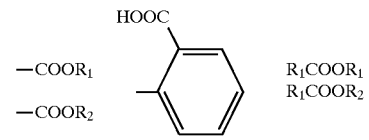

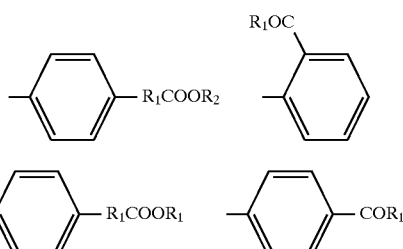

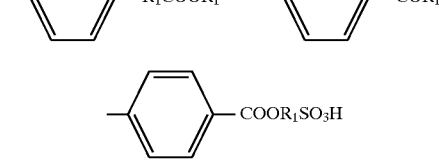

wherein $R_1$ is selected from the group consisting of $C_{1-12}$ alkyl, $C_{1-12}$ alkenyl, $C_{1-12}$ alkylene, and $C_{1-12}$ alkenylene, and wherein $R_2$ is selected from the group consisting of H, $C_{1-6}$ alkylene-$NR_1R_1$, and $C_{1-6}$ alkenylene-$NR_1R_1$, and wherein said composition contains an amount of said compound sufficient to produce direct negative chronotropic and/or negative inotropic cardioinhibitory effects.

10. A pharmaceutical composition comprising a compound having the following formula

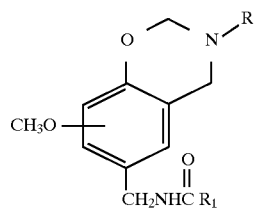

wherein R is selected from the group consisting of —$R_1$

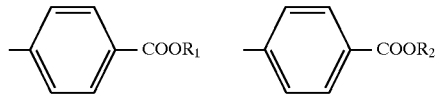

wherein $R_1$ is selected from the group consisting of $C_{1-12}$ alkyl, $C_{1-12}$ alkenyl, $C_{1-12}$ alkylene, and $C_{1-12}$ alkenylene, and wherein $R_2$ is selected from the group consisting of H, $C_{1-6}$ alkylene-$NR_1R_1$, and $C_{1-6}$ alkenylene-$NR_1R_1$, and wherein said composition contains an amount of said compound sufficient to produce tachyphylaxis.

* * * * *